(12) United States Patent
La Thangue et al.

(10) Patent No.: US 6,387,649 B1
(45) Date of Patent: *May 14, 2002

(54) ASSAY FOR A REGULATOR OF CELL CYCLE PROGRESSION

(75) Inventors: Nicholas B. La Thangue; Susana De La Luna, both of Glasgow (GB)

(73) Assignee: Prolifix Limited, Oxon (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/710,861

(22) Filed: Nov. 14, 2000

Related U.S. Application Data

(60) Division of application No. 09/189,627, filed on Nov. 10, 1998, now Pat. No. 6,159,691, which is a continuation-in-part of application No. PCT/GB97/01324, filed on May 15, 1997, which is a continuation-in-part of application No. 08/723,415, filed on Sep. 30, 1996, now Pat. No. 5,859,199.

(51) Int. Cl.$^7$ ............................................... C12Q 1/02

(52) U.S. Cl. .......................................................... 435/29

(58) Field of Search .......................................... 435/29

(56) References Cited

U.S. PATENT DOCUMENTS

| 5,859,199 A | 1/1999 | La Thangue et al. |
| 6,159,691 A | 12/2000 | La Thangue et al. |

FOREIGN PATENT DOCUMENTS

| WO | WO 93/15227 | 8/1993 |
| WO | WO 63/23539 | 11/1993 |
| WO | WO 94/10307 | 5/1994 |
| WO | WO 94/12521 | 6/1994 |
| WO | WO 96/01425 | 1/1996 |
| WO | WO 97/02354 | 1/1997 |
| WO | WO 97/43647 | 11/1997 |

OTHER PUBLICATIONS

Magae et al., Journal of Cell Science, vol. 109, pp. 1717–1726.
Ngo et al., "The Protein Folding Problem and Tertiary Structure Prediction", 1994, Mertz et al. (eds), Birkhauser, Boston, MA, pp. 433 and 492–495.
Altmann et al, TIBS 18 11/93, pp. 429 –432.
Bandara et al, The EMBO Journal of vol. 12 No. 11 pp. 4317–4324 1993.
Bandara , The EMBO Journal vol. 13 No. 13, pp. 3104–3114, 1994.
Beijersbergen et al , Genes & Development 8:2680–2690 pp. 2680–2690.
Boulikas , J. Cellular Biochemistry 55:32–58 1994.
Boulikas , Critical Reviews in Eukaryotic Gene Expression, 3(3):193–227 (1993).
Buck et al , Oncogene (1995) 11, 31–38.
Chang et al , J. of Virology 1995 vol. 69 No. 2 pp. 801–808.
Cobrinik et al, Genex & Development 7:2392–2404 1993.
Descombes et al , Cell, vol. 67 569–579 Nov. 1991.
Dingwall et al , TIBS 16 12/91 4780481.
Dynlacht et al , Genes & Development 1994 pp. 1772–1786.
Fields et al , Letters to Nature vol. 340 pp. 245–246 1989.
Flemington et al , Proc. Natl. Acad. Sci. USA vol. 90 pp. 6914–6918 1993.
Geballe et al , TIBS 19 1994 pp. 159–164.
Ginsberg et al , Genes & Development 8:2665–2679 1994.
Girling et al , Nature vol. 362 1993 pp. 83–87.
Girling et al , Molecular Biology of the Cell vol. 5, 1081–1092, 1994 pp. 1081–1092.
Helin et al , Cell vol. 70, 337–350 1992.
Helin et al , Genes & Development 7:1850–1861 1993.
Molecular and Cell Biology vol. 13, No. 10, 1993 p. 6501–6508.
Hiebert et al., Gene & Development 6:177–185 1992.
Hill et al., J. Biological Chemistry 1993 vol. 268, No. 1, Jan 5 issue pp. 726–731.
Hill et al., Cell 1995 pp. 199–211.
Hoyle et al., Molecular and Cellular Biology vol. 13, No. 12 1993, pp. 7802–7812.
Kaeline et al., vol. 70, pp. 351–364, 1992.
Kozak , Nucleic Acids Research vol. 15, No. 10 1987 pp. 8125–8148.
Krek et al., Cell vol. 78 161–172 1994.
Krek et al., Science vol. 262 1993 pp. 1557–1560.
La Thangue., TIBS 19 1994 pp. 108–114.
Lam et al., Current Opinion in Cell Biology 1994, 6:859–866.
Ormondroyd et al., Oncogene 1995, 11, 1437–1446.
Lees et al., Molecular and Cellular biology, 1993, pp. 7813–7825.
Lees et al., Genes & Development 6:1874–1885.
Li et al., Genes & Development 1993 pp. 2366–2377.
Science vol. 258, 1992 Nevins E2F: A Link between the Rb Tumor Suppressor Protein and Viral Oncoproteins.
Schwarz et al. "Interactions of the p107 and Rb proteins..." The EMBO Journal vol. 12 No. 3 pp. 1013–1020 1993.
Bei Shan et al. "Molecular Cloning of Cellular Genes..." Molecular and Cellular Biology 1992 vol. 12, pp. 5620–5631.
Shirodkar "The Transcription Factor E2F Interacts with the Retinoblastoma Product.." Cell vol. 68, 157–166. 1992.
Smith et al. "Single step purification of polypeptides expressed in *Escherichia coli* . . . " Gene 67 1988 31–40.

(List continued on next page.)

Primary Examiner—Terry McKelvey
(74) Attorney, Agent, or Firm—Nixon & Vanderhye P.C.

(57) ABSTRACT

The present invention provides nuclear localisation signals derived from the DP-3 and E2F-1 transcription factors and the use of these signals in assays for regulators of cell cycle progression. Such assays involve using the signals to direct a marker gene to the nucleus and determining whether the nuclear localisation of the marker is disrupted by the presence of a putative regulator.

1 Claim, 1 Drawing Sheet

OTHER PUBLICATIONS

Treacy et al, "Twin of I–POU: A Two Amino Acid Difference int he I–POU . . . " Cell vol. 68, 491–505 1992.

Webster et al. pp. 1441–1446 The Transcriptional activation function located in the hormone–binding domain of Weinberg, "The Retinoblastoma Protein and Cell Cycle Control" Cell, vol. 81 323–330, 1995.

Wu et al, "In vivo Assoc. of E2F and DP . . . " Molecular and Cellular Biology, vol. 15, No. 5, 1995 pp. 2536–2546.

Zamanian et al, "Adenovirus E1a prevents the . . . " The EMBO Journal, vol. 11, No. 7, pp. 2603–2610 1992.

Zamanian et al. "Transcriptional Repression by the RB . . . " Molecular Biology of the Cell, vol. 4, 389–396, 1993.

Zhang et al., "Cloning and characterization of human DP2, a novel . . . " Oncogens, 1995, 10 pp. 2085–2093.

Zhu et al., Inhibition of cell proliferation by p. 107, a relative of the retinoblastoma protein Berendsen, Science, vol. 282: pp. 642–643.

Thomas et al., "Elevated Recombination Rates in Transcriptionally Active DNA" Cell, 1989, pp. 619–630.

ASSAY FOR A REGULATOR OF CELL CYCLE PROGRESSION

This application is a divisional of U.S. application Ser. No. 09/189,627, filed Nov. 10, 1998, now U.S. Pat. No. 6,159,691, which is a continuation-in-part of PCT/GB97/01324, filed May 15, 1997, which is a continuation-in-part of U.S. application Ser. No. 08/723,415, filed Sep. 30, 1996, now U.S. Pat. No. 5,859,199, which claims benefit of GB 9610195.1, filed May 15, 1996, the entire content of which is hereby incorporated by reference in this application.

The present invention relates to the use of the E region of the transcription factor DP-3 as a target for novel assays and its use as a nuclear localisation signal.

The orderly progress of cells through the cell cycle involves a number of control points which assess the status of the intracellular and extracellular environment. A major control point, occurring as cells enter S phase, involves the cellular transcription factor E2F, a molecular implicated in the regulation of S phase gene expression (Nevins, 1992; La Thangue, 1994; Müller, 1995; Weinberg, 1995). An important for E2F in early cell cycle control is suggested by the nature of the proteins which influence its transcriptional activity. for example, members of the group of pocket proteins, exemplified by the retinoblastoma tumour suppressor gene product (pRb), repress the transcriptional activity of E2F (Hiebert et al., 1992: Zamanian and La Thangue, 1992; 1993; Schwarz et al., 1993; Wolf et al., 1995). The ability to repress E2F correlates with the capacity of pRb, or its relatives, to negatively regulate early cell cycle progression (Hiebert et al., 1992; Zamanian and Le Thangue, 1992; Hinds et al., 1992; Zhe et al., 1995; 1995a). Furthermore, growth arrest caused by high level expression of pRb can be overcome by increasing the level of E2F (Zhu et al., 1993), implying than E2F is a principal physiological target through which pRb exerts its effects on the cell cycle. Another groups of molecules which regulate cell cycle transitions, the cyclins and their associated catalytic regulatory subunits, also interact with and control the activity of E2P (Bandara et al., 1991; Lees et al., 1992; Zhu et al., 1995b). Cyclins A. E. and D together with an appropriate catalytic subunit can influence the biological activity of pocket proteins (Hinds et al., 1992; Dowdy et al., 1993; Ewen et al., Sherr, 1993), and direct phosphorylation by cyclinA-cdk2 is believed to interfere with the DNA binding activity of E2F (Krek et al., 1994; 1995).

The physiological regulation of E2F activity imparted by these afferent signalling proteins can be subverted by viral oncoproteins, such as adenovirus E1a, human papilloma virus E7 and SV40 large T antigen, through their ability to release active E2F by sequestering pocket proteins and cyclin/cdk complexes (Bandara and La Thange, 1991; Chellappan et al., 1991; 1992; Morris et al., 1993). This property correlates with the ability of these viral oncoproteins to transform tissue culture cells, again implicating E2F as an important physiological target in virally-medicated oncogensis.

Considerable progress has been made in elucidating the composition of E2F. It is now known the E2F DNA binding activity defined in mammalian cells extracts is a generic activity caused by an array of DNA binding heterodimers made up from two distinct families of proteins, known as E2F and DP (La Thangue, 1994). Five members of the E2F family, from E2F-1 to E2F-5, have been isolated, each protein possessing preferential specificity for pocket proteins (Helin et al., 1992; Kaelin et al., 1992; Shan et al 1992; Ivey-Hoyle et al., 1993; Lees et al., 1993; Beijersbergen et al., 1994; Ginsberg et al., 1994; Buck et al., 1995; Hijmans et al., 1995; Sardet et al., 1995). For example, E2F-1 is regulated by pRb, and E2F-4 by p107 and p130 (Helin et al., 1993a; Flemington et al., 1993; Beijersbergen et al., 1994; 1995; Ginsberg et al., 1994; Vairo et al., 1995). Three members of the DP family are known (Girling et al., 1993; 1994; Ormondroyd et al., 1995; Wu et al., 1995; Zhang and Chellappan, 1995), DP-1 being a widespread and constitutive component of physiological E2F during cell cycle progression in some cell types (Girling et al., 1993; Bandara et al., 1994). Supporting their role as dominant regulators of the cell cycle, both E2F and DP proteins have been shown to possess proto-oncogenic activity (Johnson et al., 1994; Jooss et al., 1995).

Our previous characterisation of DP-3 indicated that it is a novel member of the DP family of proteins and that its RNA undergoes extensive alternative splicing (Ormondroyd et al., 1995). Processing events in the 5' untranslated region and coding sequence of the RNA give rise to a rage of products present in both cell lines and tissues (Ormondroyd et al., 1995). A sequence of 16 amino acid resides within the N-terminal region of the DNA binding domain, known as the E region, is one such region subject to the alternative splicing of DP-3 RNA. Further, in the four DP-3 protein products which have been characterised, α and δ constitute E- forms, whereas β and γ are E- variants (Ormondroyd et al., 1995). although E-; extensive sequence conservation is apparent across the DP protein family, a comparison of the known DP protein sequences indicated that they fall into two categories, being either E- or for example, DP-1 is an E-variant.

DISCLOSURE OF THE INVENTION

Figure 1:
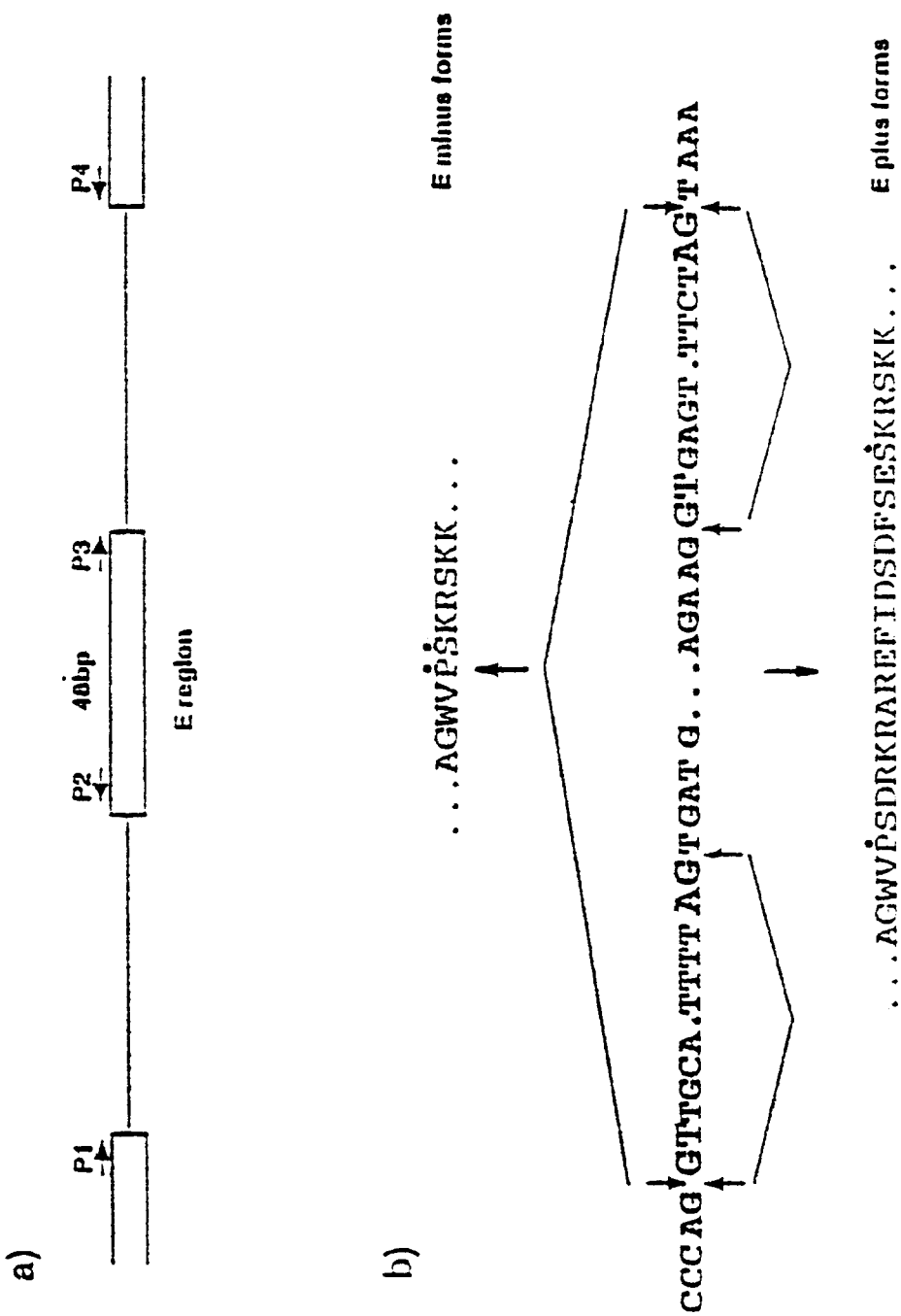
FIGS. 1(a)–1(b) show the DP-3 E-region exon and the patterns of alternate splicing which give rise to E+ and E− forms of DP-3 (SEQ ID NOS:22 to 25).

In the present study, we have defined a role for the E region by showing that its inclusion contributes to an alternatively spliced nuclear localization signal: specifically, E- DP-3 proteins accumulate in the nuclei whereas E- proteins, including DP-1, fail to do so. Without the E region, DP proteins rely upon an alternative mechanism which involves an interation with an appropriate E2F family member, for example E2F-1, for nuclear accumulation. These data define two mechanisms of control in the nuclear accumulation of E2P transcription factor influenced by alternative splicing of a nuclear localization signal and subunit composition, and indicate a hitherto unexpected and novel level of control in regulating the levels of the nuclear E2F/DP heterodimer.

The present invention thus provides an assay for a putative regulator of cell cycle progression which comprises:

a. expressing in a cell a protein comprising (i) an E region and sufficient C-terminal residues thereof of a DP-3 protein to provide a functional nuclear localisation signal (NLS) and (ii) a marker for nuclear localization; and b. determining the degree of nuclear localization in the presence and absence of said putative regulator.

In a further embodiment of the invention, the finding that DP proteins such as DP-1 lack an NLS indicate that the complex of such DP proteins with an E2F (such as E2F-1) are localised in the nucleus by the presence of an NLS on the E2F protein. The DP-3 NLS is not homologous to the E2F NLS. Thus the E2F NLS forms a further target for antagonists of nuclear localisation of the DP/E2F complex, particularly complexes such as DP-1/E2F-1 which do not comprise an E region. We have identified the nuclear localisation signal region in E2F-1. This region is identified as residues 85–91 of the human E2F-1 sequence shown as SEQ ID NO. 12 below. Thus the invention also provides an assay for a putative regulator of cell cycle progression which comprises:

a. expressing in a cell a protein comprising (i) the nuclear localisation signal of E2F-1 and (ii) a marker for nuclear localization; and b. determining the degree of nuclear localization in the presence and absence of said putative regulator.

The proteins defined in parts "a" above will be referred to as the "a protein comprising an NLS-region" and the like for the sake of brevity.

In one embodiment, the E region comprises the sequence:

S D R K R A R E F I D S D F S E    (SEQ ID NO. 9):

However, this E region is derived from the murine DP-3 gene and other E regions may be used, for example the human E region or other mammalian E regions. The murine DP-3 alpha (SEQ ID NO:1 and SEQ ID NO:2) beta (SEQ ID NO:3 and SEQ ID NO:4) gamma (SEQ ID NO: 5 and SEQ ID NO:6) and delta (SEQ ID NO:7 and SEQ ID NO:8) genes are provided herein. Other DP-3 genes may be obtained by routine cloning methods. For example, the human DP-3 gene may be cloned by probing a cDNA or genomic library with a nucleic acid probe derived from either a known human DP-gene (e.g. DP-1) and/or the murine DP-3 gene, and positive clones selected and sequenced for the human DP-3 gene. Similar techniques may be used for other mammalian DP-3 genes and will be readily apparent to those of skill in the art.

As described herein, the E region requires a number of C-terminal residues found in the DP-3 sequence in order to function as an NLS. Desirably, from 6 to 50, e.g. 8 to 30 and preferably from 8 to 20 C-terminal residues are used.

Similarly, the NLS of E2F-1 may be used with accompanying N- or C-terminal residues from the natural sequence of this protein, although these are not essential for the activity of the NLS.

Although assays of the invention are preferably based upon naturally occurring NLS-regions sequences and associated C-terminal regions thereof sufficient to act as an NLS, these sequences may also be modified by substitution, deletion or insertion provided that the function of these sequences is substantially retained. The retention of function may be tested for in accordance with the description and examples herein. Such modified and functional NLS-regions are included within the definition of the terms "an E region of a DP-3 protein" and "the nuclear localisation signal of E2F-1".

For example, from 1 to 4 substitutions may be made and these are preferably conservative substitutions. Examples of conservative substitutions include those set out in the following table, where amino acids on the same block in the second column and preferably in the same line in the third column may be substituted for each other.

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |
| OTHER | | N Q D E |

Where deletions or insertions are made, these are preferably limited in number for example from 1 to 3 of each.

The cell in which the assay may be conducted is any suitable eukaryotic cell in which the NLS-regions function as nuclear locatisation signals. Suitable cell types include yeast, insert or mammalian cells, e.g. primate cells such as COS7 cells.

In the assay according to the invention the marker may be any polypeptide sequence which allows detection of the presence and location (i.e., cytoplasmic vs nuclear) of the protein comprising an NLS region. Suitably markers include an antigenic determinant bindable by an antibody, an enzyme capable of causing a colour change to a substrate or a luciferase enzyme.

In a preferred embodiment, the marker comprises a transcription factor or subunit thereof, which transcription factor is capable of activating an indicator gene. This embodiment avoids the need for detailed examination of the cell to determine where the marker has located. In this embodiment the activation of transcription of the indicator gene will show that the NLS-regions have been located the protein in the nucleus.

For example, in a preferred embodiment of the invention the protein may comprise a heterologous DNA binding domain such as that of the yeast transcription factor GAL 4. The GAL 4 transcription factor comprises two functional domains. These domains are the DNA binding domina (DBD) and the transcriptional activation domain (TAD). By fusing an NLS-region to one of those domains and expressing the other domain in the cell, a functional GAL 4 transcription factor is restored only when two proteins enter the nucleus and interact. Thus, interaction of the proteins may be measured by the use of an indicator gene linked to a GAL 4 DNA binding site which is capable of activating transcription of said reporter gene. This assay former is described by Fields and Song, 1989, Nature 340; 245–246. Other transcriptional activator domains may be used in place of the GAL4 TAD, for example the viral VP16 activation domain (Fields and Jang, 1990). In general, fusion proteins comprising DNA binding domains and/or activation domains may be made.

The indicator gene may comprise, for example, chloramphenicol acetyl, transferase (CAT) or a luciferase.

The NLS may be located at the C-terminal or N-terminal of the marker gene. The NLS may be within all or part of the DP-3 or E2F protein from which it originates, or may be solely the NLS sequences identified above which provide the necessary NLS function. Thus fragments of DP-3 or an E2F (e.g. E2F-1) of from 15 to 400, eg from 20 to 100 or from 30 to 50 amino acids comprising the NLS may be used. Where the NLS is fused to the N- or C-terminus of a marker gene, the fusion may comprise further sequences at its N- or C-terminus where this is desired or necessary.

In any format, the assay may be used to screen peptides which regulate the function of an NLS. Regulation of the function includes antagonising the function to prevent nuclear localisation although regulators may also be agonists which enhance localisation. Regulation of the NLS may lead to effects such as enhanced cell division, blocking of cell cycle progression or apoptosis, the latter two being particularly preferred. Candidate regulators identified in accordance with the invention maybe tested on cells with wild=type DP and E2F proteins to confirm the effect of regulating the NLS.

Such regulators will be useful either in themselves as potential regulators of cell proliferation or as models for rational drug design, e.g. by modelling the tertiary structure of the antagonist and devising chemical analogues which mimic the structure.

Candidate regulators include peptides comprising all or part of a sequence which is from 60 to 100% homologous (identical) to a portion of an NLS region of the same length. Extracts of plants which contain several characterised or uncharacterised components may also be used.

Antibodies directed to the NLS regions form a further class of putative regulator compounds. Candidate regulator antibodies may be characterised and their binding regions determined to provide single chain antibodies and fragments thereof which are responsible for regulating the interaction.

Other candidate regulator compounds may be based on modelling the 3-dimensional structure of the NLS regions and using rational drug design to provide potential inhibitor compounds with particular molecular shape, size and charge characteristics.

An regulator substance identified using the present invention may be peptide or non-peptide in nature. Non-peptide "small molecules" are often preferred for many in vivo pharmaceutical uses. Accordingly, a mimetic or mimick of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g., peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding size and/or charge, using data from a range of sources, e.g., spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesis, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can than be carried out to arrive at one or more final mimetics for in vivo or clinical testing.

Antibodies may be obtained using techniques which are standard in the art. Methods of producing antibodies include immunising a mammal (e.g., mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modifies in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Examples of antibody fragments, capable of binding an antigen or other binding partner are the Fab fragment consisting of the VL, VH, Cl and CHl domains; the Pd fragment consisting of the VH and CHl domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Simple chain Fv fragments are also included.

A hybridima producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

The amount of a putative regulator which may be screened in the assay of the invention desirably will be selected to be a concentration which is within 100 fold (above or below; the amount of an NLS-region-containing protein in the cell. By way of guidance this will man that typically, from about 0.01 to 100 nM concentrations of putative regulator compound may be used, for example from 0.1 to 10 nM.

The assay of the invention may be conducted using transient expression vectors or stably transfected cells. In either case, the protein comprising an NLS-region will be encoded by nucleic acid (preferably DNA) and said nucleic acid will be operably linked to a promoter which is functional in the host cell. The promoter and nucleic acid encoding the protein comprising an NLS-region will usually be part of a vector construct which may also contain signals for termination of transcription, a selectable marker and/or origins of replication functional in the host cell and/or in another cell type (e.g., E.coli) so that the vector may be manipulated and grown in the other cell type.

Where an NLS-region sequence contains substitutions, delections or insertions as described above the alterations to the sequence may be made by manipulation of the nucleic acid sequence to alter the relevant codon(s). This can be achieved by a number of well known standard techniques, e.g. site directed mutagenesis.

Various vectors of this type are described in the Examples herein, and further vectors may be made by those of skill in the art in accordance with routine practice in molecular biology.

In a separate embodiment, the invention also provides a method of directing expression of a protein in a cell to the nucleus which comprises modifying said protein such that is comprises an NLS-region and, in the case of a DP-1 derived NLS, sufficient C-terminal residues there of a DP-3 protein to provide a functional nuclear localisation signal (NLS).

Such a method may be used to modify a DP-protein which does not normally comprise an E region so that the DP-protein (e.g., DP-1 or DP-2 does localise to the nucleus. This can be used to study the function of such DP proteins. These proteins are novel and thus form a further aspect of the invention. Desirably the NLS used to modify a DP-protein is a DP-3 derived NLS.

E2F proteins, particularly E2F-4 and E2F-5 which lack an NLS, may also be modified by an NLS of the invention. Desirably the NLS used to modify an E3F-protein is an E2F-1-derived NLS.

Modification of such proteins will usually be achieved through the use of recombinant DNA techniques, e.g. using nucleic acid encoding an NLS-region sequence and splicing it to or into nucleic acid encoding the protein of interest. The recombinant nucleic acid may be introduced into an expression vector in a manner analogous to that described above and the vector introduced into a suitable host cell, e.g. a host cell in which a promoter operably linked to the recombinant DNA coding sequence is capable of driving expression of the DNA. Suitable cell types include those described above.

The present invention also comprises an assay for a putative regulator of cell cycle progression which comprises
  a. expressing in a cell (i) an E-DP transcription factor or a portion thereof sufficient to form a heterodimer with an E2F transcription factor and (ii) an E2F transcription factor or portion thereof sufficient to form a heterodimer with the DP transcription factor or portion thereof and direct localisation of said heterodimer to the nucleus; and
  b. determining the degree of nuclear localization in the presence and absence of said putative regulator.

The assay may be performed under conditions and within cell types as described above for the assay of an NLS-region regulator, and candidate regulators include those described above for the other assays of the invention.

In this assay, a preferred DP transcription factor is DP-1, particularly mammalian DP-1, e.g. rodent or primate, e.g. human. The sequences of human and mouse DP-1 are shown in SEQ ID NO: 10 and SEQ ID NO:11, respectively. A preferred E2F is E2F-1, particularly mammalian E2F-1 (SEQ ID No:12), respectively e.g., rodent or primate, e.g. human.

Where a portion of an E- DP transcription factor is used in such an assay, it may be of any size which is capable of forming a heterodimer with an E2F transcription factor. Portions of from 40 to 400, preferably 60 to 200 amino acids may be made by routine recombinant DNA techniques and tested in system analogous to those described above and below in the accompanying examples for their ability to function as required. The portions of the DP protein will generally include substantially all or most of the domain found at amino acids 160 to 220 in DP-1 which is responsible for dimerisation with E2F-1. Where a portion of an E2F transcription factor sufficient to form a heterodimer with the DP transcription factor is used, this may also be made and tested as described above for the portion of the DP factor, and preferably is within the same size ranges and also comprises substantially all or most of the heterodimersation domain.

The following examples illustrate the invention.

EXAMPLE 1

The proteins encoded by the spliced variants of DP-3 have distinct intracellular distributions.

The DP-3 gene gives rise to a number of distinct proteins resulting from alternative splicing of its RNA (Ormondroyd et al., 1995). Since the DNA binding and transcription activation properties of the DP-3 variants, referred to as $\alpha$, $\beta$, $\gamma$ and $\delta$, are not significantly different (Ormondroyd et al., 1995) we considered that the variation within the DP-3 coding sequence may influence other properties of the proteins, such as their biochemical properties. We therefore compared the biochemical extraction properties of $\beta$ and $\delta$, which constitute E– and E+ forms respectively, after sequential treatment with increasing salt concentration and monitoring the levels of protein extracted from transfected COS7 cells.

COS7 cells were trasfected with plasmids carrying the full length coding sequences of DP-3 $\alpha$, $\beta$, $\gamma$ and $\delta$ (Ormondroyd et al., 1995) which were cloned into pG4mpoliII (Webster et al., 1989) under the control of the SV40 early prometer. pG4DP-3$\alpha\Delta$E mutant was constructed by substituting a Bsgl fragment from DP-3$\beta$ (E-minus) into DP-3$\alpha$. A number of other vectors made in connection with other examples are descirbed here for the sake of brevity: The luciferase expression vector pGL-2 was supplied by Promega, and pGL-E vector derived from pGL-2 by an inframe insertion of a 54 bp Kbal fragment encoding the 16 amino acid residue E region in a single Kbal site in the luciferase coding region. To generate pGL-Eb, a PCR fragment was amplified using E5-K (5'-GCTCTAGAGCCCAGTATAGA-3' (SEQ ID NO: 14)) and E3-X (5'-GCTCTAGATGTCTCAAGCCTTTCCC-3' (SEQ IDNO: 15)) as primers, pG4DP-3$\alpha$ (Ormondroyd et al., 1995) as the template and cloned into the single Xbal site in pGL-2. pG4-DP-1 has been already described (Bandara et al., 1993) and pRcCMV-HAE2F1 (Krek et al., 1994), expressing HA-tagged human E2F-1 was a gift of Dr W Krek. pCMV-DP-1/NLS was made by inserting a fragment containing the Bel 1 bi-partite NLS (amino acid residue 194 to 227) amplified by PCR into the Kpnl site (residue 327) of the DP-1 cDNA in pG4-DP-1. The nature of all the constructions were confirmed through sequence analysis.

The cells were grown in Dulbecco's modified Eagle's medium supplemented with 10% foetal calf serum (FCS). Cells were transfected by the liposome-mediated method, using the Lipofectin reagent (Gibco BRL) and according to maufacturer's recommendations. Sixty hours after transfection, cells were lysed in ice cold low salt buffer (LSB; 10 mM Tris-HCl pH 8, 7.5 mM $SO4(NH_4)_2$, 1 mM EDTA, 0.025% NP-40) by using 0.2 ml of LSB per 6-cm-diameter dish Lysates were incubated in its for 5 min, and centrifuged at 3000 rpm for 3 min. The resulting pellets were resuspended in 0.2 ml of high salt buffer (HSB; 50 mM Tris-HCl pH 8, 150 mM NaCl, 5 mM EDTA, 0.5% NP-40) and centrifugated at 10,000 rpm for 5 min. Each buffers, LSB and HSB, were supplemented with protease inhibitors and 1 mM dithiothreitol. The insoluble material contained in the pellets of the last centrifugation were resuspended in 0.2 ml of SDS-sample buffer.

Usually, about 5% of the different fractions was used in immunoblotting. Samples were separated on a 10% SDS-polyacrylamide gel and transferred to nitrocellulose membranes. The membrane was blocked with 5% dried milk powder in PBS for 1 h, anti-DP-3 antibody (1:200, rabbit serum) was added and incubated for additional 1 h at room temperature. After three washes in PBS with 0.2% Tween-20, the blot was incubated with alkaline phosphatase-conjugated goat anti-rabbit IgG (1:7500, Promega) for 1 h at room temperature, washed three times in PBS-0.2% Tween 20 and developed. Anti serum 7.5, raised against a peptide containing DEEDEEEDPSSPE (SEQ ID NO: 16) derived from DP-3, was used in the immunoblotting experiments.

The initial treatment with low salt (0.01M) releases mostly soluble cytoplasmic proteins, the high slat (0.5M) both nuclear and cytoplasmic, the insoluble material remaining being collected in fraction designated P. When cells expressing the β variant were treated according to this regime and the levels of β monitored by immunoblotting, it was found to be present throughout the fractions, being moderately enriched in the low salt fraction. In contrast, when cells expressing δ were treated in a similar fashion, the δ protein was far more enriched in the P fraction. Thus, the extraction properties of β and δ are different, and the E region (the only difference between β and δ proteins) is responsible for these differences.

It was possible that the differences in biochemical properties reflected distinct intracellular distributions of the DP-3 proteins. To test this idea we expressed each of the variants in COS7 cells and determined their intracellular location by immunostaining using anti-DP-3 7.2, an antiserum useful for this purpose since it only recognises the exogenous DP-3 protein. For the immunofluorescences, cells were grown on coverslips in 3 cm diameter dishes.

When either the α, β, γ or δ variant was expressed in COS7 cells, their intracellular distribution fell into two distinct categories: α and δ accumulated in nuclei whereas β and γ were distributed throughout the cytoplasm with a low level staining in nuclei. Although the α and δ proteins were exclusively nuclear, within a transfected culture of asynchronous cells minor variation was apparent in the distribution of β and γ proteins. For example, β and γ were usually present at higher levels in the cytoplasm relative to nuclei although occasional cells (less than 5% of transfected cells) were seen in which the proteins were present at similar levels in both the nucleus and the cytoplasm, a possible explanation for these observations being suggested later. In summary, these data establish that the differences in protein sequence between the variants influences their intracellular distribution. Specifically, the presence of the E regions in α and δ, but not β and γ, correlates with the ability of the protein to efficiently accumulate in nuclei.

The immunofluorescence was performed as follows. Transfected cells were fixed in 4% formaldehyde, rinsed and permeabilized in phosphate-buffered saline (PBS) containing 1% Triton X-100. Fixed cells were blocked in PBS containing 1% FCS, incubated with the primary antibodies diluted in PBS-1% FCS for 30 min at room temperature, washed three times with PBS and incubated with the secondary antibodies diluted in PBS-10% FCS for 30 min at room temperature. After a final wash with PBS, the coverslips were mounted on slides using Citofluor and examined with a Zeiss microscope. Magnification was 630× unless otherwise indicated.

As primary antibodies were used a rabbit polyclonal serum raised against a DP-3 specific peptide common to all the DP-3 variants called 7.2, a rabbit polyclonal serum which detects luciferase (Promega), a DP-1 antiserum (098) raised against a C-terminal peptide in DP-1 and the anti-HA monoclonal antibody 12CAS (BabCO). Secondary antibodies were goat anti-rabbit IgG conjugated to fluorescein isothiocyanate (1:200, FITC) and goat anti-mouse IgG conjugated to tetramethylrhodamine isothiocyanate (1:200, TRITC) (Southern biotechnology Associates Inc.). Anti-peptide serum 7.2 was raised against the sequence VALATGQLPASNSHQ (SEQ ID NO: 17) common to all DP-3 proteins.

EXAMPLE 2

The E Region is Necessary for Nuclear Localization

Since the only difference between the β and δ protein is the 16 amino acid residue E region, the E region must be necessary for the nuclear accumulation of δ. To test this idea, we removed the E region from the α variant (which like δ accumulates in nuclei) to create αΔE, and compared the intracellular distribution of the mutated protein to that of wild-type α by immunofluorescence in transfected COS7 cells as described above. The results indicated that in the absence of the E region the intracellular distribution of αΔE was altered to one which resembled the distribution of β since it failed to efficiently accumulate in nuclei. These data support the implications from the previous studies on a requirement for the E region in efficient nuclear accumulation, and thus suggest that it may function as or contribute to a nuclear localization signal (NLS).

EXAMPLE 3

An Extended E Region Functions as a Nuclear Localization Signal

An NLS can be experimentally defined by its deletion causing a loss of nuclear accumulation or by transferring the phenotype to a non nuclear protein. The previous results indicate that the properties of the E region are compatible with the first statement. To address the second, we attached the E region or an extended E region containing an additional 8 residues from the C-terminal boundary, onto luciferase (see Example 1 above for plasmid constructions).

When expressed in COS7 cells, wild-type luciferase was distributed throughout the cell, being marginally more abundant within the cytoplasm; the protein had a very similar distribution in all cells expressing wild-type luciferase. The insertion of the E region (pGL-E) did not significantly alter the distribution of the luciferase protein. However, when an addition 8 residues was inserted (pGL-Eb) nuclear accumulation became far more efficient. Thus, the E region together with additional residues located further on from the C-terminal boundary is necessary for efficient nuclear accumulation.

Together, these data suggest that the E region is necessary but not sufficient for the nuclear accumulation phenotype, and thus the 16 residue sequence is unlikely to contain an autonomous nuclear localization signal. Rather, the E region functions in a co-operative fashion with an additional part of the protein located at the C-terminal boundary of the E region to confer nuclear accumulation. In this respect, the insertion of the E region may produce a bi-partite nuclear localization signal characteristic of many eukaryotic nuclear proteins, such as nucleoplasmin (Dingwall and Laskey, 1991).

EXAMPLE 4

The E Region is Encoded by an Alternatively Spliced Exon

Although it was very likely that the presence of the E region is regulated by alternative splicing, it was not clear whether a discrete exon encoded the 16 amino acid residues. To clarify this question we isolated the DP-3 gene and characterised its genomic organization across the region encoding the E sequence. For this, a genomic library prepared from murine embryonic stem cells was screened with the DP-3 cDNA, positive clones isolated and thereafter the relationship between genomic and cDNA sequence established.

A λGEM12 genomic library prepared from embryonic stem cell line SV129D3 was plated (approximately $10^6$ pfu) and transferred to Hybond N (Amersham International). Filters were hybridised in quikHyb solution (Stratagene) at 65° C. with a $^{32}$P labelled mouse DP-3α cDNA (Ormondroyd et al, 1995). A positive genomic clone which contained the genomic E region was identified via southern blotting using a radiolabelled oligonucleotide antisense to the E region (358–4078 bp DP-3α). A genomic fragment containing the E exon was then cloned into pBluescript (pBS, Stratagene) and sequenced using a Sequenase version 2.0 kit (UBS). Oligonucleotides for PCR and sequencing were made from E+ mouse DP-3 cDNA sequences (Ormondroyd et al, 1995). Oligonucleotide sequences were as follows: 5' of E region, 7.16 5' CACCCGCAATGGTCACT-3' (SEQ ID NO: 18), 3' of E region, 7.17A; 5'-ATGTCTCAAGCCTTTCCC-3' (SEQ ID NO: 20), 3' end of E region, E2-A; 5'-TTCTGAGAAATCAGAGTCTA-3' (SEQ ID NO: 21).

The analysis indicated that the 16 residues which constitute the E region are indeed encoded by a single 48 bp exon. Conventional splica acceptor and donor sites exist for the boundaries of the E exon which, in turn, lead into two large introns and, subsequently, exon sequence encoding the surrounding DP-3 protein. This isolation and characterisation of the DP-3 gene indicated that the E region is encoded by a discrete alternatively spliced exon. This is illustrated further in FIG. 1.

EXAMPLE 5

DP-1 Lacks an Autonomous Nuclear Localization Signal

A comparison of the E region of DP-3 with the same region of DP-1 indicated that DP-1 lacks a domain analogous to E (Ormondroyd et al, 1995). Furthermore, extensive searches to isolate alternatively spliced DP-1 mRNAs have so far failed and thus we investigated the intracellular location of exogenous DP-1 when expressed in COS7 cells, using methods essentially as described above.

The DP-1 protein had a similar distribution to the β and γ (E− minus) forms of DP-3, since it was located throughout the cytoplasm with occasional low level staining in nuclei, such a result being entirely compatible with the absence of the E region. The absence of DP-1 in nuclei was due to the lack of a NLS since the exogenous DP-1 could efficiently accumulate in nuclei after attaching a foreign nuclear localization signal (NLS), the bi-partite signal taken from the Bel 1 protein (Chang et al., 1995). These data suggest that DP-1 is not actively retained in the cytoplasm but rather its cytoplasmic location is passive.

EXAMPLE 6

E2F-1 Can Recruit DP-1 and Cytoplasmic DP-3 Proteins to Nuclei

The result of Example 5 suggests that the cytoplasmic location of exogenous DP-1 is passive. We reasoned that in the absence of an autonomous NLS a possible mechanism to promote the nuclear accumulation of DP-1 may involve an interaction with its physiological partner, namely the E2F-1 protein. To test this idea, we studied the location of the E2F-1 protein in COS7 cells and thereafter the effect of co-expressing E2F-1 and DP-1 in the same cells.

An E2F-1 protein tagged at its N-terminal with a haemagglutinin (HA) epitope and visualised by immunostaining with an anti-HA monoclonal antibody was exclusively nuclear. The assess the influence of E2F-1 on DP-1, both proteins were co-expressed and their intracellular distribution determined by double immunostaining with anti-HA monoclonal antibody and rabbit anti-DP-1. Neither the fluorescein-congugated anti-rabbit immunoglobulin or rhodamine-congugated anti-mouse immunoglobulin cross-reacted with the anti-HA monoclonal antibody or the rabbit anti-DP-1 respectively.

There was a striking difference in the distribution of DP-1 upon co-expression of E2F-1: cells expressing the E2F-1 protein contained nuclear DP-1, in contrast to its cytoplasmic location in the absence of E2F-1. In the rare exceptions where the transfected cells expressed only DP-1 (about 1% of total transfected population) the exogenous DP-1 was cytoplasmic. These data strongly suggest that upon forming a DP-1/E2F-1 heterodimer, E2F-1 has a dominant influence on recruiting DP-1 to a nuclear location.

We assessed if E2F-1 had a similar effect on DP-3β and αΔE. Co-expression of DP-3 β and αΔE with E2F-1 resulted in nuclear recruitment. The presence of DP-1 or DP-3β in nuclei is likely therefore to be dependent upon an interaction with the appropriate E2F heterodimeric partner which subsequently causes the efficient nuclear accumulation of DP proteins.

EXAMPLE 7

E2F-1 Contains an NLS

The ability of E2F-1 to recruit DP-1 to the nucleus was investigated further to identify the E2F-1 NLS. Various experiments are used for this purpose. Deletion mutants of E2F-1 are made and are tested for their ability to recruit DP-1 to the nucleus. Experiments indicate that the NLS of E2F-1 (SEQ ID NO: 12) is located at residues 85–91.

DISCUSSION

Part A: Summary

The transport of macromolecules between the cytoplasm and nucleus is mediated in both directions by supramolecular structures which span the nuclear envelope called the nuclear pore complexes (NPCs). Although small macromolecules (less than 40–60 kD) can diffuse through NPCs, karyophillic proteins of any size are imported by a selective two-step mechanism which is energy dependent (Fabre and Hurt, 1994; Melchior and Gerase, 1995). Active transport of proteins into the nucleus is dependent upon short stretches of amino acid residues, known as nuclear localization signals (NLS) and, although consensus NLS sequences have been difficult to define, they frequently consist of clusters of basic residues which may be continuous or bi-partite in nature (Dingwall and Laskey, 1991; Boulikas, 1993).

Since transcription factors exert their effects on gene expression within the nucleus, it is possible that their activity could be regulated through a control of intracellular location. Mechanisms have been described which influence nuclear accumulation in response to a specific signal, such as direct post-translational modification of the transcription factor, dissociation of an inhibitory subunit which masks the NLS and interaction with a nuclear localizing protein (Whiteside and Goodbourn, 1993). Well documented examples occur in the NF-κB/Rel family of proteins, where proteclytic cleavage of a cytoplasmid precursor or an interaction with cytoplasmic IκB and related proteins controls nuclear accumulation of the functional transcription factor (Siebenlist et al., 1995; Norris and Manley, 1995). The glucocorticoid receptor is held in the cytoplasm by virtue of an interaction with heat shock protein 90, and hormone binding widely believed to promote nuclear entry by dissociating the receptor —hsp90 complex (Evans, 1988). In this study, we have documented for the first time mechanisms mediated at the level of intracellular location which influence the nuclear accumulation of the E2F heterodimer.

Part B: An alternatively spliced nuclear localization signal in the E2F transcription factor The E2F transcription factor lays an important role in integrating cell cycle progression with transcription (Neveins, 1992; La Thangue, 1994; Müller, 1995; Weinberg, 1995). In physiological E2F members of two distinct families of proteins, DP and E2F, interact as DP/E2F heterodimers (Bandara et al., 1993), with the functional consequences being co-poerative DNA binding, pocket protein binding and transcriptional activation (Bandara et al., 1993; Helin et al., 1993a; Krek et al., 1993). A number of different levels of control are known to be exerted upon the E2F heterodimer, such as binding and transcriptional repression by the pocket proteins (Helin et al., 1993b; Flemington et al., 1993), phosphorylation by cdk complexes (Krek et al., 1994; 1995) and transcriptional activation by MDM2 oncoprotein (Martin et al., 1995). Here, we have described an additional mechanism of control in regulating the activity of E2F mediated at the level of intracellular location. Specifically, our data show that two alternative mechanisms exist which control the nuclear accumulation of the DP/E2F heterodimer regulated, firstly, by alternative splicing and, secondly, subunit composition of the heterodimer.

These conclusions relate to previous observations made on the DP-3 gene which encodes a number of discrete mRNAs that arise through alternative splicing. (Ormondroyd et al., 1995). One of these processing events determines whether the E region is incorporated in the protein. Here, we show that the E region is encoded by an alternatively spliced exon which, together with an additional C-terminal extension, can confer efficient nuclear accumulation. The E region therefore contributes to a nuclear localization signal.

Interestingly, comparison of the sequence of the sixteen amino acid residues within the E region to other previously defined NLSs suggests a closer resemblance to a bi-partite NLS rather than the NLS characteristic of SV40 large T antigen (Dingwall and Laskey, 1991). Although there is some similarity to the SV40 large T antigen-like NLS, neither the sequence nor the functional properties of the E region completely satisfy the requirements for this type of NLS (Boulikas, 1993; 1994). for example, the consensus core sequence for an SV40 large T-like motif is likely to consist of at least four arginine and lysine residues, whereas the cluster within the E region consists of three basic residues. Secondly, acidic residues are rarely included within the signal sequence, yet the E region cluster contains an asparate residue embedded within it.

Functional evidence for this idea was obtained by determining if the E region is necessary and sufficient for nuclear accumulation. Although necessary in the context of wild-type DP-3 sequence, alone the E region was not sufficient to confer onto a non-nuclear resident efficient nuclear accumulation, but rather required an additional region located immediately C-terminal of the E region. This sequence, together with the cluster of basic residues within the E region, has a similar arrangement and characteristics for a bi-partite NLS namely, two basic clusters of amino acid residues separated by a spacer region (Dingwall and Laskey, 1991; La Casse and LeFebvre, 1995). In the DP-3 variants β and γ which lack in the E region, the N-terminal half of the bi-partite signal is removed by the splicing of the E exon.

The role of alternative splicing as a mechanism for generating protein isoforms with different functional properties has been widely described. The inclusion of sequences which function as NLSs has been reported in several cases, such as in the nuclear mitotic apparatus (NuMA) protein (Tang et al., 1994), CaM kinase (Srinivasan et al., 1994) and deoxynucleotidyl transferase (Bentolila et al., 1995). An interesting situation occurs in the Max gene, which encodes a heterodimeric partner for Myc, where Max RNA is alternatively spliced to result in a Max protein truncated at the C-terminus and lacking of NLS (Makela et al., 1992). In contrast to wild-type Max, the truncated Max protein enhances the transformation activity of Myc (Makela et al; 1992). Nevertheless, a physiological splicing event which regulates a bi-partite NLS in such a fashion by removing one of the clusters of basic residues is, to our knowledge, novel. Thus, these data define a previously unidentified level of control in the E2F transcription factor and could, more generally, indicate a new mechanism for regulating the activity of bi-partite NLSs through RNA processing.

Although these data establish a dependence upon the E region for nuclear accumulation, they do not distinguish between the possibilities that the E region regulates nuclear entry or export. For example, it is possible that E– variants can enter and exit nuclei, and that the presence of the E region impedes nuclear export, resulting in a net nuclear accumulation. Such a possibility would be compatible with the altered biochemical extraction properties confired by the E region, which suggested that the E region may be involved in tethering to an insoluble nuclear structure. Interestingly, pRb is believed to be held in the nucleus by a tethering process, a property characteristic of the hypophosphorylated protein and thus potentially important in mediating physiological effects of cell cycle arrest (Mittnacht et al., 1991).

Part C: Heterodimer Formation Between DP and E2F Family Members Provides a Mechanism for Efficient Nuclear Accumulation The DP-3β and γ variants fail to accumulate in nuclei when expressed in COS7 cells, a phenotype which can now be directly attributed to the absence of the E region. The DP-1 protein, which lacks a region analogous to E (Girling et al, 1993; Ormondroyd et al, 1995), behaved in a fashion predicted for an E-DP variant since exogenous DP-1 protein on COS7 cell shad a similar location as the DP-3 E-variants.

The distribution of the E– DP variants, which are predominantly cytoplasmic, could result from one of several scenarios. For example, passive diffusion may occur such that at equilibrium in proteins are more abundant within the cytoplasm. Alternatively, the proteins may have a weak NLS which fails to efficiently target them to nuclei, a possibility consistent with the E– variants still possessing one half of the bi-partite NLS and observations made on the nucleoplasmin NLS where elimination of one half of the bi-partite signal does not completely abolish nuclear accumulation (Robbins et al., 1991). Finally, it is also possible that the cytoplasmic pattern results from an active retention mechanism. However, this latter possibility is unlikely since a heterologous NLS was sufficient to confer a nuclear accumulation phenotype.

We reasoned that there must be physiological mechanisms which promote the efficient nuclear accumulation of DP-1 given that the endogenous DP-1 is nuclear (data not shown). We therefore tested whether formation of a DP/E2F heterodimer was involved in such a mechanism, experiments which indicated that co-expression of E2F-1 recruited E– DP proteins to nuclei, and thus heterodimerization with an appropriate E2F family member is likely to be sufficient to promote nuclear accumulation. Mechanistically, the nuclear accumulation of E-DP variants upon an interaction with E2F-1 may occur if E2F-1 is tethered within the nucleus and, upon interacting with DP variants, causes their retention in the nucleus. Alternatively, the interaction with E2F-1 may occur within the cytoplasm and the physical interaction with E2F-1 be responsible for delivering E– DP variants to the nucleus. Overall, these data suggest two distinct mechanisms for the nuclear accumulation of DP proteins, one dependent on the presence of an intrinsic sequence in the protein and the other on an interaction with the appropriate E2F partner.

The fact that heterodimer formation can promote nuclear accumulation provides a likely explanation for the small proportion of COS7 cells which contain exogenous nuclear β protein. We suggest in such cells that β has a nuclear location by virtue of an interaction and heterodimer formation with endogenous E2F proteins.

Part D: Physiological Implications

A mechanism through which nuclear accumulation is dependent upon heterodimerization has a number of important implications for the regulation of functional E2F transcription factor, that is, the DP/E2F heterodimer. For example, it would favour the presence of DP/E2F heterodimers, the physiological form involved in transcriptional activation (Bandara et al., 1993; Helin et al., 1993b; Krek et al., 1993), in nuclei perhaps preventing some non-specific and/or undesirable interactions occurring. It may, in addition, provide a mechanism whereby the induction of nuclear DP/E2F heterodimers is dependent on a rate limiting E2F partner. Indeed, the expression of the E2F-1 gene is known to be under cell cycle control, in contrast to DP-1 which in some cell types is constitutively expressed during the cell cycle (Slansky et al., 1993). In such a model, although DP-1 is expressed its contribution to transcriptional activation in the context of the DP/E2F heterodimer during the cell cycle will be strictly dependent upon the levels of E2F-1.

We have established that the E region of DP proteins is required for nuclear accumulation, and that it likely functions as a bi-partite nuclear localization signal. Although this situation is novel, as yet we do have to understand the role that this mechanism plays in physiological E2F and the regulation of cell cycle progression. It is possible, we suggest, the E+ variants of DP proteins function in an analogous fashion as E2F-1 for DP-1 to recruit proteins capable of interacting with E+ variants but which lack an autonomous nuclear localization signal.

In conclusion, this study has highlighted a new and unexpected mechanism of control in regulating the activity of the E2F heterodimer. Specifically, nuclear accumulation is dramatically influenced by two distinct levels of control: alternative splicing of an exon which contributes to a nuclear localization signal and the subunit composition of the E2F heterodimer. It is likely that this control plays an important role in regulating the activity of the E2F transcription factor and hence cell cycle progression.

REFERENCES

Bandara, L. R. and La Thangue, N. B. (1991). *Nature* 351: 494–497.

Bandara, L. R., et al (1991). *Nature* 352: 249–251.

Bandara, L. R., Buck, V. M., Zamanian, M., Johnston, L. H. and La Thangue, N. B. (1993). *EMBO J.* 12, 4317–4324.

Bandara, L. R., Lam, E. W. -F., Sørensen, T. S., Zamanian, M., Girling, R. and La Thangue, N. B. (1994). *EMBO J.* 13, 3104–3114.

Beijersbergen, R. L., Kerkhoven, R. M., Zhu, L., Carlee, L., Voorhoeva, P. M. and Bernards, R. (1994). *Genes. Dev.* 8, 2680–2690.

Beijersbergen, R. L., et al (1995). *Genes Dev.* 9: 1340–1353.

Bentolila, L. A. et al (1995). *EMBO J.* 14: 4221–4229.

Boulikas, T. (1993). *Crit. Rev. Eukar. Gene Expr.* 3: 193–227.

Boulikas, T. (1994). *J. Cell Biochem.* 55: 32–38.

Boulikas, T. (1993). *Crit. Rev. Eukar. Gene Expr.* 3: 193–227.

Buck, V., Alien, E. K., Sørensen, T., Bybee, A., Hijmans, E. M., Voorhoeve, P. M., Bernards, R. and La Thangue, N. B. (1995). *Oncogene,* 11, 31–39.

Chang, J., Lee K. J., Jang, K. L., Lee, E. K., Baek, G. H. and Sung, Y. C. (1995). *J. Virology* 69: 801–808.

Chellappan, S. P. et al (1991). *Cell* 65: 1053–1061.

Chellappan, S., et al (1992). *Proc. Natl. Acad. Sci. USA* 89: 4549–4553.

Dingwall, C. and Laskey, R. (1991). *Trends. Biochem. Sci* 16: 478–481.

Dowdy, S. F. et al (1993). *Cell* 73: 499–511.

Evans, R. M. (1988). *Science* 240: 889–895.

Ewen, M. E. et al (1993). *Cell* 73: 487–497.

Fabre, E. and Hurt, E. C. (1994). *Cur. Op. Cell Biol.* 6: 335–342.

Flemington, E. K., Speck, S. H. and Kaelin, W. G. (1993). *Proc. Natl. Acad. Sci. USA.* 90, 6914–6918.

Ginsberg, D., Vairo, G., Chittenden, T., Xiao, X. -X., Xu. G., Wydner, K. L., DeCaprio, J. A., Lawrence, J. B. and Livingston, D. M. (1994). *Genes. Dev.* 8, 2665–2679.

Girling, R., Partridge, J. F., Bandara, L. R., Burden, N., Totty, N. F., Hsuan, J. J. and La Thangue, N. B. (1993). *Nature* 362, 83–87.

Girling, R., Bandara, L. R., Ormondroyd, E., Lam, E. W. -F., Kotecha, S., Mohun, T. and La Thangue, N. B. (1994). *Mol. Biol. Cell.* 5, 1081–1092.

Heibert, S. W., Chellappan, S. P., Horowitz, J. M. and Nevins, J. R. (1992). *Genes Dev.* 6, 171–185.
Helin, K., Lees, J. A., Vidal, M., Dyson, N., Harlow, E. and Fattaey, A. (1992). *Cell* 70, 337–350.
Helin, K., Wu, C. -L., Fattaey, A. R., Lees, J. A., Dynlacht, B. D., Hgwu, C. and Harlow, E. (1993b). *Genes Dev.* 7, 1850–1861.
Helin, K., Harlow, E. and Fattaey, A. R. (1993a). *Mol. Cell. Biol.* 13: 6501–6508.
Hijmans, E. M. et al (1995). *Mol. Cell. Biol.* 15: 3082–3089.
Hinds, P. W., Mittnacht. S., Dulic, V., Arnold, A., Reed, S. L. and Ivey-Hoyle, M., Conroy, R., Huber, H. E., Goodhart, P. J., Cliff, A. and Heimbrook, D. C. (1993). *Mol. Cell. Biol.* 13, 7802–7812.
Ivey-Hoyle, M. et al (1993). *Mol. Cell. Bio.* 13: 7802–7812.
Johnson, D. G. et al (1994). *Proc. Natl. Acad. Sci. USA* 91: 12823–12827.
Jooss, K. et al (1995). *Oncogene* 10: 1529–1536.
Kaelin, W. G., Krek, W., Sellers, W. R., DeCaprio, J. A., Ajchenbaum, F., Fuchs, C. S., Chittenden, T., Li, Y., Farnham, P. J., Blanar, M. A., Livingston, D. M. and Flemington, E. K. (1992). *Cell* 70, 351–364.
Krek, W., Ewen, M. E., Shirodkar, S., Arany, Z., Kaelin, W. G. and Livingston, D. M. (1994). *Cell* 78, 161–172.
Krek, W., Livingston, D. M. and Shirodkar, S. (1993). *Science* 262, 1557–1560.
Krek, W. et al (1995). *Cell* 83: 1149–1158.
La Casse, E. C. and Lefebvre, Y. A. (1995). *Nuc. Ac. Res.* 23: 1647–1656.
La Thangue, N. B. (1994). *Trends Biochem. Sci.* 19, 108–114.
Lees, J. A., Saito, M., Vidal, M., Valentine, M., Lock, T., Harlow, E., Dyson, N. and Helin, K. (1993). *Mol. Cell. Biol.* 13, 7813–7825.
Lees, E., Faha, B., Dulic, V., Reed, S. I. and Harlow, E. (1992). *Genes Dev.* 6, 1874–1885.
Makela, T. P. et al (1992). *Science* 256: 373–377.
Martin, K. et al (1995). *Nature* 375: 691–694.
Melchior, F. and Gerace, L. (1995). *Cur. Op. Cell Biol.* 7: 310–318.
Mittnacht, S. and Weinberg, R. A. (1991). *Cell* 65: 381–393.
Morris, J. D. et al (1993). *Oncogene* 8: 893–898.
Müller, R. (1995). *Trends Genet.* 11: 173–178.
Nevins, J. R. (1992). *Science* 258, 424–429.
Norris, J. L. and Manley, J. L. (1995). *Inducible Gene Expression*, Vol. 2, 243–265. P. A. Baeuerle, Ed. Birkhauser Boston.
Ormondroyd, E., de la Luna, S. and La Thangue, N. (1995) *Oncogene* 11, 1437–1446.
Robbins, J. et al. (1991). *Cell* 64: 615–623.
Sardet, C. et al (1995). *Proc. Natl. Acad. Sci. USA* 92: 2403–2407.
Schwarz, J. K., Devoto, S. H., Smith, E. J., Chellappan, S. P., Jakoi, L. and Nevins, J. R. (1993). Interactions of the p107 and Rb proteins with E2F during the cell proliferation response. *EMBO J.* 12: 1013–1020.
Shan, B., Zhu, X., Chen, P. L., Durfee, T., Yang, Y., Sharp, D. and Lee, W. H. (1992). *Mol. Cell. Biol.* 12, 5620–5631.
Sherr, C. J. (1993). Mammalian G1 cyclins. *Cell* 73: 1059–1065.
Siebenlist, U. et al (1995). *Inducible Gene Expression*, Vol. 1, 93–141. P. A. Baeuerle, Ed. Birkhaüser Boston.
Slansky, J. E. et al (1993). *Mol. Cell. Biol.* 13: 1610–1618.
Srinivasan, M. et al (1994). *J. Cell. Biol.* 126: 839–852.
Tang, T. K et al (1994). *J. Cell Sci.* 107: 1389–1402.
Vairo, G. et al (1995). *Genes Dev.* 9: 869–881.
Webster, N. J. G., Green, S., Tasset, D., Ponglikitmongkol. MN. and Chambon, P. (1989). *EMBO. J.* 8: 1441–1446.
Weinberg, R. A. (1995). *Cell* 81: 323–330.
Whiteside, S. T. and Goodbourn, S. (1993). *J. Cell Sci.* 104: 949–955.
Wolf, D. A. et al (1995). *Oncogene* 10: 2067–2078.
Wu, C. -L., Zukerberg, L. R., Ngwu, C., Harlow, E. and Lees, J. A. (1995). *Mol. Cell. Bio.* 15, 2536–2546.
Zamanian, M. and La Thangue, N. B. (1992). *EMBO J.* 11, 2603–2610.
Zamanian, M. and La Thangue, N. B. (1993). *Mol. Biol. Cell.* 4, 389–396.
Zhang, Y. and Chellappan, S. (1995). *Oncogene,* 10, 2085–2093.
Zhu, L., Van Der Heurel, S., Helin, K., Fattaey, A., Ewen, M., Livingston, D., Dyson, N. and Harlow, E. (1993). *Genes Dev.* 7, 1111–1125.
Zhu, L. et al (1995a). *EMBO J.* 14: 1904–1913.
Zhu, L. et al (1995b). *Genes Dev.* 9: 1740–1752.

---

SEQUENCE LISTING

<160> NUMBER OF SEQ ID NOS: 25

<210> SEQ ID NO 1
<211> LENGTH: 1385
<212> TYPE: DNA
<213> ORGANISM: mouse
<220> FEATURE:
<221> NAME/KEY: CDS
<222> LOCATION: (1)..(1338)

<400> SEQUENCE: 1

```
atg acg gca aaa aat gtt ggt ttg cca tcc a ca aat gca gag ctg agg      48
Met Thr Ala Lys Asn Val Gly Leu Pro Ser T hr Asn Ala Glu Leu Arg
  1               5                  10                  15 ggc ttt ata gat cag aat ttc agt cca acg a aa ggt aac att tca ctt      96
Gly Phe Ile Asp Gln Asn Phe Ser Pro Thr L ys Gly Asn Ile Ser Leu
             20                  25                  30 gtt gcc ttt cca gtt tca agc acc aac tca c ca aca aag att tta ccg     144
```

```
Val Ala Phe Pro Val Ser Ser Thr Asn Ser P ro Thr Lys Ile Leu Pro
         35                  40                 45 aaa acc tta ggg cca ata aat gtg aat gtt g ga ccc caa atg att ata      192
Lys Thr Leu Gly Pro Ile Asn Val Asn Val G ly Pro Gln Met Ile Ile
     50                  55                 60 agc aca ccg cag aga att gcc aat tca gga a gt gtt ctg att ggg aat      240
Ser Thr Pro Gln Arg Ile Ala Asn Ser Gly S er Val Leu Ile Gly Asn
 65              70                  75                  80 cca tat acc cct gca ccc gca atg gtc act c ag act cac ata gct gag      288
Pro Tyr Thr Pro Ala Pro Ala Met Val Thr G ln Thr His Ile Ala Glu
                 85                  90                  95 gct gct ggc tgg gtt ccc agt agt aga aaa c ga gct aga gaa ttt ata      336
Ala Ala Gly Trp Val Pro Ser Ser Arg Lys A rg Ala Arg Glu Phe Ile
             100                 105                 110 gac tct gat ttt tca gaa agt aaa cga agc a aa aaa gga gat aaa aat      384
Asp Ser Asp Phe Ser Glu Ser Lys Arg Ser L ys Lys Gly Asp Lys Asn
         115                 120                 125 ggg aaa ggc ttg aga cat ttt tca atg aag g tg tgt gag aaa gtt cag      432
Gly Lys Gly Leu Arg His Phe Ser Met Lys V al Cys Glu Lys Val Gln
 130             135                 140 cgg aaa ggc aca act tca tac aat gag gta g ct gat gag ctg gta tct      480
Arg Lys Gly Thr Thr Ser Tyr Asn Glu Val A la Asp Glu Leu Val Ser
145             150                 155                 160 gag ttt acc aac tca aat aac cat ctg gca g ct gat tcg gct tat gat      528
Glu Phe Thr Asn Ser Asn Asn His Leu Ala A la Asp Ser Ala Tyr Asp
                 165                 170                 175 cag gag aac att aga cga aga gtt tat gat g ct tta aat gta cta atg      576
Gln Glu Asn Ile Arg Arg Arg Val Tyr Asp A la Leu Asn Val Leu Met
             180                 185                 190 gcg atg aac ata att tca aag gaa aaa aaa g aa atc aag tgg att ggc      624
Ala Met Asn Ile Ile Ser Lys Glu Lys Lys G lu Ile Lys Trp Ile Gly
         195                 200                 205 ctg cct acc aat tct gct cag gaa tgc cag a ac ctg gaa atc gag aag      672
Leu Pro Thr Asn Ser Ala Gln Glu Cys Gln A sn Leu Glu Ile Glu Lys
 210             215                 220 cag agg cgg ata gaa cgg ata aag cag aag c ga gcc cag cta caa gaa      720
Gln Arg Arg Ile Glu Arg Ile Lys Gln Lys A rg Ala Gln Leu Gln Glu
225             230                 235                 240 ctt ctc ctt cag caa att gct ttt aaa aac c tg gta cag aga aat cga      768
Leu Leu Leu Gln Gln Ile Ala Phe Lys Asn L eu Val Gln Arg Asn Arg
                 245                 250                 255 caa aat gaa caa caa aac cag ggc cct cca g ct gtg aat tcc acc att      816
Gln Asn Glu Gln Gln Asn Gln Gly Pro Pro A la Val Asn Ser Thr Ile
             260                 265                 270 cag ctg cca ttt ata atc att aat aca agc a gg aaa aca gtc ata gac      864
Gln Leu Pro Phe Ile Ile Ile Asn Thr Ser A rg Lys Thr Val Ile Asp
         275                 280                 285 tgc agc atc tcc agt gac aaa ttt gaa tac c tt ttt aat ttt gat aac      912
Cys Ser Ile Ser Ser Asp Lys Phe Glu Tyr L eu Phe Asn Phe Asp Asn
 290             295                 300 acc ttt gag atc cac gac gac ata gag gta c tg aag cgg atg gga atg      960
Thr Phe Glu Ile His Asp Asp Ile Glu Val L eu Lys Arg Met Gly Met
305             310                 315                 320 tcc ttt ggt ctg gag tca ggc aaa tgc tct c tg gag gat ctg aaa atc     1008
Ser Phe Gly Leu Glu Ser Gly Lys Cys Ser L eu Glu Asp Leu Lys Ile
                 325                 330                 335 gca aga tcc ctg gtt cca aaa gct tta gaa g gc tat att aca gat atc     1056
Ala Arg Ser Leu Val Pro Lys Ala Leu Glu G ly Tyr Ile Thr Asp Ile
             340                 345                 350
```

```
tcc aca gga cct tct tgg tta aat cag gga c ta ctt ttg aac tct acc      1104
Ser Thr Gly Pro Ser Trp Leu Asn Gln Gly L eu Leu Leu Asn Ser Thr
            355                 360                 365 caa tca gtt tca aat tta gac ccg acc acc g gt gcc act gta ccc caa      1152
Gln Ser Val Ser Asn Leu Asp Pro Thr Thr G ly Ala Thr Val Pro Gln
        370                 375                 380 tca agt gta aac caa ggg ttg tgc ttg gat g ct gaa gtg gcc tta gca      1200
Ser Ser Val Asn Gln Gly Leu Cys Leu Asp A la Glu Val Ala Leu Ala
385                 390                 395                 400 act ggg cag ctc cct gcc tca aac agt cac c ag tcc agc agt gca gcc      1248
Thr Gly Gln Leu Pro Ala Ser Asn Ser His G ln Ser Ser Ser Ala Ala
                405                 410                 415 tct cac ttc tcg gag tcc cgc ggc gag acc c cc tgt tca ttc aac gat      1296
Ser His Phe Ser Glu Ser Arg Gly Glu Thr P ro Cys Ser Phe Asn Asp
            420                 425                 430 gaa gat gag gaa gat gaa gag gag gat ccc t cc tcc cca gaa              1338
Glu Asp Glu Glu Asp Glu Glu Glu Asp Pro S er Ser Pro Glu
        435                 440                 445 taaagacagg agagaactca tgtttttaaaa aaaaaaaaaa actcgag                    1385

<210> SEQ ID NO 2
<211> LENGTH: 446
<212> TYPE: PRT
<213> ORGANISM: mouse

<400> SEQUENCE: 2

Met Thr Ala Lys Asn Val Gly Leu Pro Ser T hr Asn Ala Glu Leu Arg
  1               5                  10                  15

Gly Phe Ile Asp Gln Asn Phe Ser Pro Thr L ys Gly Asn Ile Ser Leu
             20                  25                  30

Val Ala Phe Pro Val Ser Ser Thr Asn Ser P ro Thr Lys Ile Leu Pro
         35                  40                  45

Lys Thr Leu Gly Pro Ile Asn Val Asn Val G ly Pro Gln Met Ile Ile
     50                  55                  60

Ser Thr Pro Gln Arg Ile Ala Asn Ser Gly S er Val Leu Ile Gly Asn
 65                  70                  75                  80

Pro Tyr Thr Pro Ala Pro Ala Met Val Thr G ln Thr His Ile Ala Glu
                 85                  90                  95

Ala Ala Gly Trp Val Pro Ser Ser Arg Lys A rg Ala Arg Glu Phe Ile
            100                 105                 110

Asp Ser Asp Phe Ser Glu Ser Lys Arg Ser L ys Lys Gly Asp Lys Asn
        115                 120                 125

Gly Lys Gly Leu Arg His Phe Ser Met Lys V al Cys Glu Lys Val Gln
    130                 135                 140

Arg Lys Gly Thr Thr Ser Tyr Asn Glu Val A la Asp Glu Leu Val Ser
145                 150                 155                 160

Glu Phe Thr Asn Ser Asn Asn His Leu Ala A la Asp Ser Ala Tyr Asp
                165                 170                 175

Gln Glu Asn Ile Arg Arg Val Tyr Asp Ala L eu Asn Val Leu Met
            180                 185                 190

Ala Met Asn Ile Ile Ser Lys Glu Lys Lys G lu Ile Lys Trp Ile Gly
        195                 200                 205

Leu Pro Thr Asn Ser Ala Gln Glu Cys Gln A sn Leu Glu Ile Glu Lys
    210                 215                 220

Gln Arg Arg Ile Glu Arg Ile Lys Gln Lys A rg Ala Gln Leu Gln Glu
225                 230                 235                 240
```

```
Leu Leu Leu Gln Gln Ile Ala Phe Lys Asn Leu Val Gln Arg Asn Arg
                245                 250                 255

Gln Asn Glu Gln Gln Asn Gln Gly Pro Pro Ala Val Asn Ser Thr Ile
            260                 265                 270

Gln Leu Pro Phe Ile Ile Ile Asn Thr Ser Arg Lys Thr Val Ile Asp
        275                 280                 285

Cys Ser Ile Ser Ser Asp Lys Phe Glu Tyr Leu Phe Asn Phe Asp Asn
    290                 295                 300

Thr Phe Glu Ile His Asp Asp Ile Glu Val Leu Lys Arg Met Gly Met
305                 310                 315                 320

Ser Phe Gly Leu Glu Ser Gly Lys Cys Ser Leu Glu Asp Leu Lys Ile
                325                 330                 335

Ala Arg Ser Leu Val Pro Lys Ala Leu Glu Gly Tyr Ile Thr Asp Ile
            340                 345                 350

Ser Thr Gly Pro Ser Trp Leu Asn Gln Gly Leu Leu Leu Asn Ser Thr
        355                 360                 365

Gln Ser Val Ser Asn Leu Asp Pro Thr Thr Gly Ala Thr Val Pro Gln
    370                 375                 380

Ser Ser Val Asn Gln Gly Leu Cys Leu Asp Ala Glu Val Ala Leu Ala
385                 390                 395                 400

Thr Gly Gln Leu Pro Ala Ser Asn Ser His Gln Ser Ser Ser Ala Ala
                405                 410                 415

Ser His Phe Ser Glu Ser Arg Gly Glu Thr Pro Cys Ser Phe Asn Asp
            420                 425                 430

Glu Asp Glu Glu Asp Glu Glu Asp Pro Ser Ser Pro Glu
        435                 440                 445

<210> SEQ ID NO 3
<211> LENGTH: 1154
<212> TYPE: DNA
<213> ORGANISM: mouse
<220> FEATURE:
<221> NAME/KEY: CDS
<222> LOCATION: (1)..(1107)

<400> SEQUENCE: 3 atg att ata agc aca ccg cag aga att gcc aat tca gga agt gtt ctg      48
Met Ile Ile Ser Thr Pro Gln Arg Ile Ala Asn Ser Gly Ser Val Leu
  1               5                  10                  15 att ggg aat cca tat acc cct gca ccc gca atg gtc act cag act cac      96
Ile Gly Asn Pro Tyr Thr Pro Ala Pro Ala Met Val Thr Gln Thr His
             20                  25                  30 ata gct gag gct gct ggc tgg gtt ccc agt aaa cga agc aaa aaa gga     144
Ile Ala Glu Ala Ala Gly Trp Val Pro Ser Lys Arg Ser Lys Lys Gly
         35                  40                  45 gat aaa aat ggg aaa ggc ttg aga cat ttt tca atg aag gtg tgt gag     192
Asp Lys Asn Gly Lys Gly Leu Arg His Phe Ser Met Lys Val Cys Glu
     50                  55                  60 aaa gtt cag cgg aaa ggc aca act tca tac aat gag gta gct gat gag     240
Lys Val Gln Arg Lys Gly Thr Thr Ser Tyr Asn Glu Val Ala Asp Glu
 65                  70                  75                  80 ctg gta tct gag ttt acc aac tca aat aac cat ctg gca gct gat tcg     288
Leu Val Ser Glu Phe Thr Asn Ser Asn Asn His Leu Ala Ala Asp Ser
                 85                  90                  95 gct tat gat cag gag aac att aga cga aga gtt tat gat gct tta aat     336
Ala Tyr Asp Gln Glu Asn Ile Arg Arg Arg Val Tyr Asp Ala Leu Asn
            100                 105                 110 gta cta atg gcg atg aac ata att tca aag gaa aaa aaa gaa atc aag     384
```

```
tgg att ggc ctg cct acc aat tct gct cag gaa tgc cag aac ctg gaa    432
Trp Ile Gly Leu Pro Thr Asn Ser Ala Gln Glu Cys Gln Asn Leu Glu
    130                 135                 140 atc gag aag cag agg cgg ata gaa cgg ata aag cag aag cga gcc cag    480
Ile Glu Lys Gln Arg Arg Ile Glu Arg Ile Lys Gln Lys Arg Ala Gln
145                 150                 155                 160 cta caa gaa ctt ctc ctt cag caa att gct ttt aaa aac ctg gta cag    528
Leu Gln Glu Leu Leu Leu Gln Gln Ile Ala Phe Lys Asn Leu Val Gln
                165                 170                 175 aga aat cga caa aat gaa caa caa aac cag ggc cct cca gct gtg aat    576
Arg Asn Arg Gln Asn Glu Gln Gln Asn Gln Gly Pro Pro Ala Val Asn
            180                 185                 190 tcc acc att cag ctg cca ttt ata atc att aat aca agc agg aaa aca    624
Ser Thr Ile Gln Leu Pro Phe Ile Ile Ile Asn Thr Ser Arg Lys Thr
        195                 200                 205 gtc ata gac tgc agc atc tcc agt gac aaa ttt gaa tac ctt ttt aat    672
Val Ile Asp Cys Ser Ile Ser Ser Asp Lys Phe Glu Tyr Leu Phe Asn
    210                 215                 220 ttt gat aac acc ttt gag atc cac gac gac ata gag gta ctg aag cgg    720
Phe Asp Asn Thr Phe Glu Ile His Asp Asp Ile Glu Val Leu Lys Arg
225                 230                 235                 240 atg gga atg tcc ttt ggt ctg gag tca ggc aaa tgc tct ctg gag gat    768
Met Gly Met Ser Phe Gly Leu Glu Ser Gly Lys Cys Ser Leu Glu Asp
                245                 250                 255 ctg aaa atc gca aga tcc ctg gtt cca aaa gct tta gaa ggc tat att    816
Leu Lys Ile Ala Arg Ser Leu Val Pro Lys Ala Leu Glu Gly Tyr Ile
            260                 265                 270 aca gat atc tcc aca gga cct tct tgg tta aat cag gga cta ctt ttg    864
Thr Asp Ile Ser Thr Gly Pro Ser Trp Leu Asn Gln Gly Leu Leu Leu
        275                 280                 285 aac tct acc caa tca gtt tca aat tta gac ccg acc acc ggt gcc act    912
Asn Ser Thr Gln Ser Val Ser Asn Leu Asp Pro Thr Thr Gly Ala Thr
    290                 295                 300 gta ccc caa tca agt gta aac caa ggg ttg tgc ttg gat gct gaa gtg    960
Val Pro Gln Ser Ser Val Asn Gln Gly Leu Cys Leu Asp Ala Glu Val
305                 310                 315                 320 gcc tta gca act ggg cag ctc cct gcc tca aac agt cac cag tcc agc   1008
Ala Leu Ala Thr Gly Gln Leu Pro Ala Ser Asn Ser His Gln Ser Ser
                325                 330                 335 agt gca gcc tct cac ttc tcg gag tcc cgc ggc gag acc ccc tgt tca   1056
Ser Ala Ala Ser His Phe Ser Glu Ser Arg Gly Glu Thr Pro Cys Ser
            340                 345                 350 ttc aac gat gaa gat gag gaa gat gaa gag gag gat ccc tcc tcc cca   1104
Phe Asn Asp Glu Asp Glu Glu Asp Glu Glu Glu Asp Pro Ser Ser Pro
        355                 360                 365 gaa taaagacagg agagaactca tgttttaaaa aaaaaaaaaa actcgag           1154
Glu

<210> SEQ ID NO 4
<211> LENGTH: 369
<212> TYPE: PRT
<213> ORGANISM: mouse

<400> SEQUENCE: 4

Met Ile Ile Ser Thr Pro Gln Arg Ile Ala Asn Ser Gly Ser Val Leu
 1               5                  10                  15

Ile Gly Asn Pro Tyr Thr Pro Ala Pro Ala Met Val Thr Gln Thr His
                20                  25                  30
```

```
Ile Ala Glu Ala Ala Gly Trp Val Pro Ser Lys Arg Ser Lys Lys Gly
         35                  40                  45
Asp Lys Asn Gly Lys Gly Leu Arg His Phe Ser Met Lys Val Cys Glu
 50                  55                  60
Lys Val Gln Arg Lys Gly Thr Thr Ser Tyr Asn Glu Val Ala Asp Glu
 65                  70                  75                  80
Leu Val Ser Glu Phe Thr Asn Ser Asn Asn His Leu Ala Ala Asp Ser
                 85                  90                  95
Ala Tyr Asp Gln Glu Asn Ile Arg Arg Val Tyr Asp Ala Leu Asn
             100                 105                 110
Val Leu Met Ala Met Asn Ile Ile Ser Lys Glu Lys Lys Glu Ile Lys
             115                 120                 125
Trp Ile Gly Leu Pro Thr Asn Ser Ala Gln Glu Cys Gln Asn Leu Glu
         130                 135                 140
Ile Glu Lys Gln Arg Arg Ile Glu Arg Ile Lys Gln Lys Arg Ala Gln
145                 150                 155                 160
Leu Gln Glu Leu Leu Gln Gln Ile Ala Phe Lys Asn Leu Val Gln
                 165                 170                 175
Arg Asn Arg Gln Asn Glu Gln Gln Asn Gln Gly Pro Pro Ala Val Asn
             180                 185                 190
Ser Thr Ile Gln Leu Pro Phe Ile Ile Asn Thr Ser Arg Lys Thr
         195                 200                 205
Val Ile Asp Cys Ser Ile Ser Ser Asp Lys Phe Glu Tyr Leu Phe Asn
         210                 215                 220
Phe Asp Asn Thr Phe Glu Ile His Asp Asp Ile Glu Val Leu Lys Arg
225                 230                 235                 240
Met Gly Met Ser Phe Gly Leu Glu Ser Gly Lys Cys Ser Leu Glu Asp
                 245                 250                 255
Leu Lys Ile Ala Arg Ser Leu Val Pro Lys Ala Leu Glu Gly Tyr Ile
             260                 265                 270
Thr Asp Ile Ser Thr Gly Pro Ser Trp Leu Asn Gln Gly Leu Leu Leu
             275                 280                 285
Asn Ser Thr Gln Ser Val Ser Asn Leu Asp Pro Thr Thr Gly Ala Thr
         290                 295                 300
Val Pro Gln Ser Ser Val Asn Gln Gly Leu Cys Leu Asp Ala Glu Val
305                 310                 315                 320
Ala Leu Ala Thr Gly Gln Leu Pro Ala Ser Asn Ser His Gln Ser Ser
                 325                 330                 335
Ser Ala Ala Ser His Phe Ser Glu Ser Arg Gly Glu Thr Pro Cys Ser
             340                 345                 350
Phe Asn Asp Glu Asp Glu Glu Asp Glu Glu Glu Asp Pro Ser Ser Pro
         355                 360                 365
Glu
```

<210> SEQ ID NO 5
<211> LENGTH: 1157
<212> TYPE: DNA
<213> ORGANISM: mouse
<220> FEATURE:
<221> NAME/KEY: CDS
<222> LOCATION: (1)..(1110)

<400> SEQUENCE: 5

```
atg att ata agc aca ccg cag aga att gcc aat tca gga agt gtt ctg      48
Met Ile Ile Ser Thr Pro Gln Arg Ile Ala Asn Ser Gly Ser Val Leu
```

|   |   |   |   |   |   |   |   |   |   |   |   |   |   |   |   |   |
|---|---|---|---|---|---|---|---|---|---|---|---|---|---|---|---|---|
| 1 |   |   |   | 5 |   |   |   |   | 10 |   |   |   |   | 15 |   |   |

```
att ggg aat cca tat acc cct gca ccc gca a tg gtc act cag act cac      96
Ile Gly Asn Pro Tyr Thr Pro Ala Pro Ala M et Val Thr Gln Thr His
              20                  25                  30 ata gct gag gct gct ggc tgg gtt ccc agt a aa cga agc aaa aaa gga     144
Ile Ala Glu Ala Ala Gly Trp Val Pro Ser L ys Arg Ser Lys Lys Gly
     35              40                  45 gat aaa aat ggg aaa ggc ttg aga cat ttt t ca atg aag gtg tgt gag     192
Asp Lys Asn Gly Lys Gly Leu Arg His Phe S er Met Lys Val Cys Glu
 50                  55                  60 aaa gtt cag cgg aaa ggc aca act tca tac a at gag gta gct gat gag     240
Lys Val Gln Arg Lys Gly Thr Thr Ser Tyr A sn Glu Val Ala Asp Glu
 65                  70                  75                  80 ctg gta tct gag ttt acc aac tca aat aac c at ctg gca gct gat tcg     288
Leu Val Ser Glu Phe Thr Asn Ser Asn Asn H is Leu Ala Ala Asp Ser
                 85                  90                  95 cag gct tat gat cag gag aac att aga cga a ga gtt tat gat gct tta     336
Gln Ala Tyr Asp Gln Glu Asn Ile Arg Arg A rg Val Tyr Asp Ala Leu
            100                 105                 110 aat gta cta atg gcg atg aac ata att tca a ag gaa aaa aaa gaa atc     384
Asn Val Leu Met Ala Met Asn Ile Ile Ser L ys Glu Lys Lys Glu Ile
        115                 120                 125 aag tgg att ggc ctg cct acc aat tct gct c ag gaa tgc cag aac ctg     432
Lys Trp Ile Gly Leu Pro Thr Asn Ser Ala G ln Glu Cys Gln Asn Leu
130                 135                 140 gaa atc gag aag cag agg cgg ata gaa cgg a ta aag cag aag cga gcc     480
Glu Ile Glu Lys Gln Arg Arg Ile Glu Arg I le Lys Gln Lys Arg Ala
145                 150                 155                 160 cag cta caa gaa ctt ctc ctt cag caa att g ct ttt aaa aac ctg gta     528
Gln Leu Gln Glu Leu Leu Leu Gln Gln Ile A la Phe Lys Asn Leu Val
                165                 170                 175 cag aga aat cga caa aat gaa caa caa aac c ag ggc cct cca gct gtg     576
Gln Arg Asn Arg Gln Asn Glu Gln Gln Asn G ln Gly Pro Pro Ala Val
            180                 185                 190 aat tcc acc att cag ctg cca ttt ata atc a tt aat aca agc agg aaa     624
Asn Ser Thr Ile Gln Leu Pro Phe Ile Ile I le Asn Thr Ser Arg Lys
        195                 200                 205 aca gtc ata gac tgc agc atc tcc agt gac a aa ttt gaa tac ctt ttt     672
Thr Val Ile Asp Cys Ser Ile Ser Ser Asp L ys Phe Glu Tyr Leu Phe
    210                 215                 220 aat ttt gat aac acc ttt gag atc cac gac g ac ata gag gta ctg aag     720
Asn Phe Asp Asn Thr Phe Glu Ile His Asp A sp Ile Glu Val Leu Lys
225                 230                 235                 240 cgg atg gga atg tcc ttt ggt gag tca g gc aaa tgc tct ctg gag     768
Arg Met Gly Met Ser Phe Gly Leu Glu Ser G ly Lys Cys Ser Leu Glu
                245                 250                 255 gat ctg aaa atc gca aga tcc ctg gtt cca a aa gct tta gaa ggc tat     816
Asp Leu Lys Ile Ala Arg Ser Leu Val Pro L ys Ala Leu Glu Gly Tyr
            260                 265                 270 att aca gat atc tcc aca gga cct tct tgg t ta aat cag gga cta ctt     864
Ile Thr Asp Ile Ser Thr Gly Pro Ser Trp L eu Asn Gln Gly Leu Leu
        275                 280                 285 ttg aac tct acc caa tca gtt tca aat tta g ac ccg acc acc ggt gcc     912
Leu Asn Ser Thr Gln Ser Val Ser Asn Leu A sp Pro Thr Thr Gly Ala
    290                 295                 300 act gta ccc caa tca agt gta aac caa ggg t tg tgc ttg gat gct gaa     960
Thr Val Pro Gln Ser Ser Val Asn Gln Gly L eu Cys Leu Asp Ala Glu
305                 310                 315                 320 gtg gcc tta gca act ggg cag ctc cct gcc t ca aac agt cac cag tcc    1008
```

-continued

```
Val Ala Leu Ala Thr Gly Gln Leu Pro Ala S er Asn Ser His Gln Ser
                325                 330                 335 agc agt gca gcc tct cac ttc tcg gag tcc c gc ggc gag acc ccc tgt    1056
Ser Ser Ala Ala Ser His Phe Ser Glu Ser A rg Gly Glu Thr Pro Cys
            340                 345                 350 tca ttc aac gat gaa gat gag gaa gat gaa g ag gag gat ccc tcc tcc    1104
Ser Phe Asn Asp Glu Asp Glu Glu Asp Glu G lu Glu Asp Pro Ser Ser
            355                 360                 365 cca gaa taaagacagg agagaactca tgttttaaaa aaaaaaaaaa a ctcgag        1157
Pro Glu
    370

<210> SEQ ID NO 6
<211> LENGTH: 370
<212> TYPE: PRT
<213> ORGANISM: mouse

<400> SEQUENCE: 6

Met Ile Ile Ser Thr Pro Gln Arg Ile Ala A sn Ser Gly Ser Val Leu
  1               5                  10                  15

Ile Gly Asn Pro Tyr Thr Pro Ala Pro Ala M et Val Thr Gln Thr His
                 20                  25                  30

Ile Ala Glu Ala Ala Gly Trp Val Pro Ser L ys Arg Ser Lys Lys Gly
             35                  40                  45

Asp Lys Asn Gly Lys Gly Leu Arg His Phe S er Met Lys Val Cys Glu
         50                  55                  60

Lys Val Gln Arg Lys Gly Thr Thr Ser Tyr A sn Glu Val Ala Asp Glu
 65                  70                  75                  80

Leu Val Ser Glu Phe Thr Asn Ser Asn Asn H is Leu Ala Ala Asp Ser
                 85                  90                  95

Gln Ala Tyr Asp Gln Glu Asn Ile Arg Arg A rg Val Tyr Asp Ala Leu
            100                 105                 110

Asn Val Leu Met Ala Met Asn Ile Ile Ser L ys Glu Lys Lys Glu Ile
            115                 120                 125

Lys Trp Ile Gly Leu Pro Thr Asn Ser Ala G ln Glu Cys Gln Asn Leu
130                 135                 140

Glu Ile Glu Lys Gln Arg Arg Ile Glu Arg I le Lys Gln Lys Arg Ala
145                 150                 155                 160

Gln Leu Gln Glu Leu Leu Leu Gln Gln Ile A la Phe Lys Asn Leu Val
                165                 170                 175

Gln Arg Asn Arg Gln Asn Glu Gln Gln Asn G ln Gly Pro Pro Ala Val
            180                 185                 190

Asn Ser Thr Ile Gln Leu Pro Phe Ile Ile I le Asn Thr Ser Arg Lys
            195                 200                 205

Thr Val Ile Asp Cys Ser Ile Ser Ser Asp L ys Phe Glu Tyr Leu Phe
        210                 215                 220

Asn Phe Asp Asn Thr Phe Glu Ile His Asp A sp Ile Glu Val Leu Lys
225                 230                 235                 240

Arg Met Gly Met Ser Phe Gly Leu Glu Ser G ly Lys Cys Ser Leu Glu
                245                 250                 255

Asp Leu Lys Ile Ala Arg Ser Leu Val Pro L ys Ala Leu Glu Gly Tyr
            260                 265                 270

Ile Thr Asp Ile Ser Thr Gly Pro Ser Trp L eu Asn Gln Gly Leu Leu
        275                 280                 285

Leu Asn Ser Thr Gln Ser Val Ser Asn Leu A sp Pro Thr Thr Gly Ala
    290                 295                 300
```

-continued

```
Thr Val Pro Gln Ser Ser Val Asn Gln Gly Leu Cys Leu Asp Ala Glu
305                 310                 315                 320

Val Ala Leu Ala Thr Gly Gln Leu Pro Ala Ser Asn Ser His Gln Ser
            325                 330                 335

Ser Ser Ala Ala Ser His Phe Ser Glu Ser Arg Gly Glu Thr Pro Cys
        340                 345                 350

Ser Phe Asn Asp Glu Asp Glu Asp Glu Glu Glu Asp Pro Ser Ser
    355                 360                 365

Pro Glu
    370

<210> SEQ ID NO 7
<211> LENGTH: 1202
<212> TYPE: DNA
<213> ORGANISM: mouse
<220> FEATURE:
<221> NAME/KEY: CDS
<222> LOCATION: (1)..(1155)

<400> SEQUENCE: 7 atg att ata agc aca ccg cag aga att gcc aat tca gga agt gtt ctg        48
Met Ile Ile Ser Thr Pro Gln Arg Ile Ala Asn Ser Gly Ser Val Leu
  1               5                  10                  15 att ggg aat cca tat acc cct gca ccc gca atg gtc act cag act cac        96
Ile Gly Asn Pro Tyr Thr Pro Ala Pro Ala Met Val Thr Gln Thr His
                 20                  25                  30 ata gct gag gct gct ggc tgg gtt ccc agt agt aga aaa cga gct aga       144
Ile Ala Glu Ala Ala Gly Trp Val Pro Ser Ser Arg Lys Arg Ala Arg
             35                  40                  45 gaa ttt ata gac tct gat ttt tca gaa agt aaa cga agc aaa aaa gga       192
Glu Phe Ile Asp Ser Asp Phe Ser Glu Ser Lys Arg Ser Lys Lys Gly
         50                  55                  60 gat aaa aat ggg aaa ggc ttg aga cat ttt tca atg aag gtg tgt gag       240
Asp Lys Asn Gly Lys Gly Leu Arg His Phe Ser Met Lys Val Cys Glu
 65                  70                  75                  80 aaa gtt cag cgg aaa ggc aca act tca tac aat gag gta gct gat gag       288
Lys Val Gln Arg Lys Gly Thr Thr Ser Tyr Asn Glu Val Ala Asp Glu
                 85                  90                  95 ctg gta tct gag ttt acc aac tca aat aac cat ctg gca gct gat tcg       336
Leu Val Ser Glu Phe Thr Asn Ser Asn Asn His Leu Ala Ala Asp Ser
            100                 105                 110 gct tat gat cag gag aac att aga cga aga gtt tat gat gct tta aat       384
Ala Tyr Asp Gln Glu Asn Ile Arg Arg Arg Val Tyr Asp Ala Leu Asn
        115                 120                 125 gta cta atg gcg atg aac ata att tca aag gaa aaa aaa gaa atc aag       432
Val Leu Met Ala Met Asn Ile Ile Ser Lys Glu Lys Lys Glu Ile Lys
130                 135                 140 tgg att ggc ctg cct acc aat tct gct cag gaa tgc cag aac ctg gaa       480
Trp Ile Gly Leu Pro Thr Asn Ser Ala Gln Glu Cys Gln Asn Leu Glu
145                 150                 155                 160 atc gag aag cag agg cgg ata gaa cgg ata aag cag aag cga gcc cag       528
Ile Glu Lys Gln Arg Arg Ile Glu Arg Ile Lys Gln Lys Arg Ala Gln
                165                 170                 175 cta caa gaa ctt ctc ctt cag caa att gct ttt aaa aac ctg gta cag       576
Leu Gln Glu Leu Leu Leu Gln Gln Ile Ala Phe Lys Asn Leu Val Gln
            180                 185                 190 aga aat cga caa aat gaa caa caa aac cag ggc cct cca gct gtg aat       624
Arg Asn Arg Gln Asn Glu Gln Gln Asn Gln Gly Pro Pro Ala Val Asn
        195                 200                 205
```

| | | |
|---|---|---|
| tcc acc att cag ctg cca ttt ata atc att a at aca agc agg aaa aca<br>Ser Thr Ile Gln Leu Pro Phe Ile Ile Ile A sn Thr Ser Arg Lys Thr<br>210 215 220 | | 672 |
| gtc ata gac tgc agc atc tcc agt gac aaa t tt gaa tac ctt ttt aat<br>Val Ile Asp Cys Ser Ile Ser Ser Asp Lys P he Glu Tyr Leu Phe Asn<br>225 230 235 240 | | 720 |
| ttt gat aac acc ttt gag atc cac gac gac a ta gag gta ctg aag cgg<br>Phe Asp Asn Thr Phe Glu Ile His Asp Asp I le Glu Val Leu Lys Arg<br>245 250 255 | | 768 |
| atg gga atg tcc ttt ggt ctg gag tca ggc a aa tgc tct ctg gag gat<br>Met Gly Met Ser Phe Gly Leu Glu Ser Gly L ys Cys Ser Leu Glu Asp<br>260 265 270 | | 816 |
| ctg aaa atc gca aga tcc ctg gtt cca aaa g ct tta gaa ggc tat att<br>Leu Lys Ile Ala Arg Ser Leu Val Pro Lys A la Leu Glu Gly Tyr Ile<br>275 280 285 | | 864 |
| aca gat atc tcc aca gga cct tct tgg tta a at cag gga cta ctt ttg<br>Thr Asp Ile Ser Thr Gly Pro Ser Trp Leu A sn Gln Gly Leu Leu Leu<br>290 295 300 | | 912 |
| aac tct acc caa tca gtt tca aat tta gac c cg acc acc ggt gcc act<br>Asn Ser Thr Gln Ser Val Ser Asn Leu Asp P ro Thr Thr Gly Ala Thr<br>305 310 315 320 | | 960 |
| gta ccc caa tca agt gta aac caa ggg ttg t gc ttg gat gct gaa gtg<br>Val Pro Gln Ser Ser Val Asn Gln Gly Leu C ys Leu Asp Ala Glu Val<br>325 330 335 | | 1008 |
| gcc tta gca act ggg cag ctc cct gcc tca a ac agt cac cag tcc agc<br>Ala Leu Ala Thr Gly Gln Leu Pro Ala Ser A sn Ser His Gln Ser Ser<br>340 345 350 | | 1056 |
| agt gca gcc tct cac ttc tcg gag tcc cgc g gc gag acc ccc tgt tca<br>Ser Ala Ala Ser His Phe Ser Glu Ser Arg G ly Glu Thr Pro Cys Ser<br>355 360 365 | | 1104 |
| ttc aac gat gaa gat gag gaa gat gaa gag g ag gat ccc tcc tcc cca<br>Phe Asn Asp Glu Asp Glu Glu Asp Glu Glu G lu Asp Pro Ser Ser Pro<br>370 375 380 | | 1152 |
| gaa taaagacagg agagaactca tgttttaaaa aaaaaaaaaa actcgag<br>Glu<br>385 | | 1202 |

<210> SEQ ID NO 8
<211> LENGTH: 385
<212> TYPE: PRT
<213> ORGANISM: mouse

<400> SEQUENCE: 8

Met Ile Ile Ser Thr Pro Gln Arg Ile Ala A sn Ser Gly Ser Val Leu
1               5                   10                  15

Ile Gly Asn Pro Tyr Thr Pro Ala Pro Ala M et Val Thr Gln Thr His
            20                  25                  30

Ile Ala Glu Ala Ala Gly Trp Val Pro Ser S er Arg Lys Arg Ala Arg
        35                  40                  45

Glu Phe Ile Asp Ser Asp Phe Ser Glu Ser L ys Arg Ser Lys Lys Gly
    50                  55                  60

Asp Lys Asn Gly Lys Gly Leu Arg His Phe S er Met Lys Val Cys Glu
65                  70                  75                  80

Lys Val Gln Arg Lys Gly Thr Thr Ser Tyr A sn Glu Val Ala Asp Glu
                85                  90                  95

Leu Val Ser Glu Phe Thr Asn Ser Asn Asn H is Leu Ala Ala Asp Ser
            100                 105                 110

Ala Tyr Asp Gln Glu Asn Ile Arg Arg Arg V al Tyr Asp Ala Leu Asn
        115                 120                 125

-continued

```
Val Leu Met Ala Met Asn Ile Ile Ser Lys Glu Lys Lys Glu Ile Lys
    130                 135                 140
Trp Ile Gly Leu Pro Thr Asn Ser Ala Gln Glu Cys Gln Asn Leu Glu
145                 150                 155                 160
Ile Glu Lys Gln Arg Arg Ile Glu Arg Ile Lys Gln Lys Arg Ala Gln
                165                 170                 175
Leu Gln Glu Leu Leu Gln Gln Ile Ala Phe Lys Asn Leu Val Gln
            180                 185                 190
Arg Asn Arg Gln Asn Glu Gln Gln Asn Gln Gly Pro Pro Ala Val Asn
        195                 200                 205
Ser Thr Ile Gln Leu Pro Phe Ile Ile Ile Asn Thr Ser Arg Lys Thr
    210                 215                 220
Val Ile Asp Cys Ser Ile Ser Ser Asp Lys Phe Glu Tyr Leu Phe Asn
225                 230                 235                 240
Phe Asp Asn Thr Phe Glu Ile His Asp Asp Ile Glu Val Leu Lys Arg
                245                 250                 255
Met Gly Met Ser Phe Gly Leu Glu Ser Gly Lys Cys Ser Leu Glu Asp
            260                 265                 270
Leu Lys Ile Ala Arg Ser Leu Val Pro Lys Ala Leu Glu Gly Tyr Ile
        275                 280                 285
Thr Asp Ile Ser Thr Gly Pro Ser Trp Leu Asn Gln Gly Leu Leu Leu
    290                 295                 300
Asn Ser Thr Gln Ser Val Ser Asn Leu Asp Pro Thr Thr Gly Ala Thr
305                 310                 315                 320
Val Pro Gln Ser Ser Val Asn Gln Gly Leu Cys Leu Asp Ala Glu Val
                325                 330                 335
Ala Leu Ala Thr Gly Gln Leu Pro Ala Ser Asn Ser His Gln Ser Ser
            340                 345                 350
Ser Ala Ala Ser His Phe Ser Glu Ser Arg Gly Glu Thr Pro Cys Ser
        355                 360                 365
Phe Asn Asp Glu Asp Glu Asp Glu Glu Asp Pro Ser Ser Pro
    370                 375                 380
Glu
385

<210> SEQ ID NO 9
<211> LENGTH: 16
<212> TYPE: PRT
<213> ORGANISM: mouse

<400> SEQUENCE: 9

Ser Asp Arg Lys Arg Ala Arg Glu Phe Ile Asp Ser Asp Phe Glu Ser
1               5                   10                  15

<210> SEQ ID NO 10
<211> LENGTH: 410
<212> TYPE: PRT
<213> ORGANISM: human

<400> SEQUENCE: 10

Met Ala Lys Asp Ala Gly Leu Ile Glu Ala Asn Gly Glu Leu Lys Val
1               5                   10                  15

Phe Ile Asp Gln Asn Leu Ser Pro Gly Lys Gly Val Val Ser Leu Val
            20                  25                  30

Ala Val His Pro Ser Thr Val Asn Pro Leu Gly Lys Gln Leu Leu Pro
        35                  40                  45
```

-continued

Lys Thr Phe Gly Gln Ser Asn Val Asn Ile A la Gln Gln Val Val Ile
            50                      55                      60

Gly Thr Pro Gln Arg Pro Ala Ala Ser Asn T hr Leu Val Val Gly Ser
 65                      70                      75                      80

Pro His Thr Pro Ser Thr His Phe Ala Ser G ln Asn Gln Pro Ser Asp
                85                      90                      95

Ser Ser Pro Trp Ser Ala Gly Lys Arg Asn A rg Lys Gly Glu Lys Asn
                100                     105                     110

Gly Lys Gly Leu Arg His Phe Ser Met Lys V al Cys Glu Lys Val Gln
            115                     120                     125

Arg Lys Gly Thr Thr Ser Tyr Asn Glu Val A la Asp Glu Leu Val Ala
130                     135                     140

Glu Phe Ser Ala Ala Asp Asn His Ile Leu P ro Asn Glu Ser Ala Tyr
145                     150                     155                     160

Asp Gln Lys Asn Ile Arg Arg Val Tyr A sp Ala Leu Asn Val Leu
                165                     170                     175

Met Ala Met Asn Ile Ile Ser Lys Glu Lys L ys Glu Ile Lys Trp Ile
                180                     185                     190

Gly Leu Pro Thr Asn Ser Ala Gln Glu Cys G ln Asn Leu Glu Val Glu
            195                     200                     205

Arg Gln Arg Arg Leu Glu Arg Ile Lys Gln L ys Gln Ser Gln Leu Gln
            210                     215                     220

Glu Leu Ile Leu Gln Gln Ile Ala Phe Lys A sn Leu Val Gln Arg Asn
225                     230                     235                     240

Arg His Ala Glu Gln Gln Ala Ser Arg Pro P ro Pro Pro Asn Ser Val
                245                     250                     255

Ile His Leu Pro Phe Ile Ile Val Asn Thr S er Lys Lys Thr Val Ile
                260                     265                     270

Asp Cys Ser Ile Ser Asn Asp Lys Phe Glu T yr Leu Phe Asn Phe Asp
            275                     280                     285

Asn Thr Phe Glu Ile His Asp Asp Ile Glu V al Leu Lys Arg Met Gly
            290                     295                     300

Met Ala Cys Gly Leu Glu Ser Gly Ser Cys S er Ala Glu Asp Leu Lys
305                     310                     315                     320

Met Ala Arg Ser Leu Val Pro Lys Ala Leu G lu Pro Tyr Val Thr Glu
                325                     330                     335

Met Ala Gln Gly Thr Val Gly Val Phe I le Thr Thr Ala Gly Ser
            340                     345                     350

Thr Ser Asn Gly Thr Arg Phe Ser Ala Ser A sp Leu Thr Asn Gly Ala
            355                     360                     365

Asp Gly Met Leu Ala Thr Ser Ser Asn Gly S er Gln Tyr Ser Gly Ser
 370                     375                     380

Arg Val Glu Thr Pro Val Ser Tyr Val Gly G lu Asp Glu Asp Glu Asp
385                     390                     395                     400

Asp Asp Phe Asn Glu Asn Asp Glu Asp
                405                     410

<210> SEQ ID NO 11
<211> LENGTH: 410
<212> TYPE: PRT
<213> ORGANISM: mouse

<400> SEQUENCE: 11

Met Ala Lys Asp Ala Ser Leu Ile Glu Ala A sn Gly Glu Leu Lys Val

```
  1               5                   10                  15
Phe Ile Asp Gln Asn Leu Ser Pro Gly Lys G ly Val Val Ser Leu Val
                20              25              30
Ala Val His Pro Ser Thr Val Asn Thr Leu G ly Lys Gln Leu Leu Pro
            35              40              45
Lys Thr Phe Gly Gln Ser Asn Val Asn Ile T hr Gln Gln Val Val Ile
        50              55              60
Gly Thr Pro Gln Arg Pro Ala Ser Asn T hr Ile Val Val Gly Ser
65              70              75              80
Pro His Thr Pro Asn Thr His Phe Val Ser G ln Asn Gln Thr Ser Asp
                85              90              95
Ser Ser Pro Trp Ser Ala Gly Lys Arg Asn A rg Lys Gly Glu Lys Asn
            100             105             110
Gly Lys Gly Leu Arg His Phe Ser Met Lys V al Cys Glu Lys Val Gln
        115             120             125
Arg Lys Gly Thr Thr Ser Tyr Asn Glu Val A la Asp Glu Leu Val Ala
        130             135             140
Glu Phe Ser Ala Ala Asp Asn His Ile Leu P ro Asn Glu Ser Ala Tyr
145             150             155             160
Asp Gln Lys Asn Ile Arg Arg Val Tyr A sp Ala Leu Asn Val Leu
                165             170             175
Met Ala Met Asn Ile Ile Ser Lys Glu Lys L ys Glu Ile Lys Trp Ile
                180             185             190
Gly Leu Pro Thr Asn Ser Ala Gln Glu Cys G ln Asn Leu Glu Val Glu
            195             200             205
Arg Gln Arg Arg Leu Glu Arg Ile Lys Gln L ys Gln Ser Gln Leu Gln
        210             215             220
Glu Leu Ile Leu Gln Gln Ile Ala Phe Lys A sn Leu Val Gln Arg Asn
225             230             235             240
Arg Gln Ala Glu Gln Gln Ala Arg Arg Pro P ro Pro Asn Ser Val
                245             250             255
Ile His Leu Pro Phe Ile Ile Val Asn Thr S er Arg Lys Thr Val Ile
                260             265             270
Asp Cys Ser Ile Ser Asn Asp Lys Phe Glu T yr Leu Phe Asn Phe Asp
        275             280             285
Asn Thr Phe Glu Ile His Asp Asp Ile Glu V al Leu Lys Arg Met Gly
        290             295             300
Met Ala Cys Gly Leu Glu Ser Gly Asn Cys S er Ala Glu Asp Leu Lys
305             310             315             320
Val Ala Arg Ser Leu Val Pro Lys Ala Leu G lu Pro Tyr Val Thr Glu
                325             330             335
Met Ala Gln Gly Ser Ile Gly Gly Val Phe V al Thr Thr Thr Gly Ser
            340             345             350
Thr Ser Asn Gly Thr Arg Leu Ser Ala Ser A sp Leu Ser Asn Gly Ala
        355             360             365
Asp Gly Met Leu Ala Thr Ser Ser Asn Gly S er Gln Tyr Ser Gly Ser
        370             375             380
Arg Val Glu Thr Pro Val Ser Tyr Val Gly G lu Asp Asp Asp Asp
385             390             395             400
Asp Asp Phe Asn Glu Asn Asp Glu Glu Asp
                405             410
```

<210> SEQ ID NO 12

-continued

```
<211> LENGTH: 2457
<212> TYPE: DNA
<213> ORGANISM: human
<220> FEATURE:
<221> NAME/KEY: CDS
<222> LOCATION: (87)..(1397)

<400> SEQUENCE: 12
gggatcgagc cctcgccgag gcctgccgcc atgggcccgc gccgccgccg c cgcctgtca        60 cccgggccgc gcgggccgtg agcgtc atg gcc ttg gcc ggg gcc cct gcg ggc        113
                             Met Ala Leu Ala Gly Ala Pro Ala Gly
                               1               5 ggc cca tgc gcg ccg gcg ctg gag gcc ctg c tc ggg gcc ggc gcg ctg        161
Gly Pro Cys Ala Pro Ala Leu Glu Ala Leu L eu Gly Ala Gly Ala Leu
 10                  15                  20                  25 cgg ctg ctc gac tcc tcg cag atc gtc atc a tc tcc gcc gcg cag gac        209
Arg Leu Leu Asp Ser Ser Gln Ile Val Ile I le Ser Ala Ala Gln Asp
                 30                  35                  40 gcc agc gcc ccg ccg gct ccc acc ggc ccc g cg gcg ccc gcc gcc ggc        257
Ala Ser Ala Pro Pro Ala Pro Thr Gly Pro A la Ala Pro Ala Ala Gly
             45                  50                  55 ccc tgc gac cct gac ctg ctg ctc ttc gcc a ca ccg cag gcg ccc cgg        305
Pro Cys Asp Pro Asp Leu Leu Leu Phe Ala T hr Pro Gln Ala Pro Arg
         60                  65                  70 ccc aca ccc agt gcg ccg cgg ccc gcg ctc g gc cgc ccg ccg gtg aag        353
Pro Thr Pro Ser Ala Pro Arg Pro Ala Leu G ly Arg Pro Pro Val Lys
     75                  80                  85 cgg agg ctg gac ctg gaa act gac cat cag t ac ctg gcc gag agc agt        401
Arg Arg Leu Asp Leu Glu Thr Asp His Gln T yr Leu Ala Glu Ser Ser
 90                  95                 100                 105 ggg cca gct cgg ggc aga ggc cgc cat cca g ga aaa ggt gtg aaa tcc        449
Gly Pro Ala Arg Gly Arg Gly Arg His Pro G ly Lys Gly Val Lys Ser
                110                 115                 120 ccg ggg gag aag tca cgc tat gag acc tca c tg aat ctg acc acc aag        497
Pro Gly Glu Lys Ser Arg Tyr Glu Thr Ser L eu Asn Leu Thr Thr Lys
            125                 130                 135 cgc ttc ctg gag ctg ctg agc cac tcg gct g ac ggt gtc gtc gac ctg        545
Arg Phe Leu Glu Leu Leu Ser His Ser Ala A sp Gly Val Val Asp Leu
        140                 145                 150 aac tgg gct gcc gag gtg ctg aag gtg cag a ag cgg cgc atc tat gac        593
Asn Trp Ala Ala Glu Val Leu Lys Val Gln L ys Arg Arg Ile Tyr Asp
155                 160                 165 atc acc aac gtc ctt gag ggc atc cag ctc a tt gcc aag aag tcc aag        641
Ile Thr Asn Val Leu Glu Gly Ile Gln Leu I le Ala Lys Lys Ser Lys
170                 175                 180                 185 aac cac atc cag tgg ctg ggc agc cac acc a ca gtg ggc gtc ggc gga        689
Asn His Ile Gln Trp Leu Gly Ser His Thr T hr Val Gly Val Gly Gly
                190                 195                 200 cgg ctt gag ggg ttg acc cag gac ctc cga c ag ctg cag gag agc gag        737
Arg Leu Glu Gly Leu Thr Gln Asp Leu Arg G ln Leu Gln Glu Ser Glu
            205                 210                 215 cag cag ctg gac cac ctg atg aat atc tgt a ct acg cag ctg cgc ctg        785
Gln Gln Leu Asp His Leu Met Asn Ile Cys T hr Thr Gln Leu Arg Leu
        220                 225                 230 ctc tcc gag gac act gac agc cag cgc ctg g cc tac gtg acg tgt cag        833
Leu Ser Glu Asp Thr Asp Ser Gln Arg Leu A la Tyr Val Thr Cys Gln
    235                 240                 245 gac ctt cgt agc att gca gac cct gca gag c ag atg gtt atg gtg atc        881
Asp Leu Arg Ser Ile Ala Asp Pro Ala Glu G ln Met Val Met Val Ile
250                 255                 260                 265
```

-continued

| | |
|---|---|
| aaa gcc cct cct gag acc cag ctc caa gcc g tg gac tct tcg gag aac<br>Lys Ala Pro Pro Glu Thr Gln Leu Gln Ala V al Asp Ser Ser Glu Asn<br>270 275 280 | 929 |
| ttt cag atc tcc ctt aag agc aaa caa ggc c cg atc gat gtt ttc ctg<br>Phe Gln Ile Ser Leu Lys Ser Lys Gln Gly P ro Ile Asp Val Phe Leu<br>285 290 295 | 977 |
| tgc cct gag gag acc gta ggt ggg atc agc c ct ggg aag acc cca tcc<br>Cys Pro Glu Glu Thr Val Gly Gly Ile Ser P ro Gly Lys Thr Pro Ser<br>300 305 310 | 1025 |
| cag gag gtc act tct gag gag gag aac agg g cc act gac tct gcc acc<br>Gln Glu Val Thr Ser Glu Glu Glu Asn Arg A la Thr Asp Ser Ala Thr<br>315 320 325 | 1073 |
| ata gtg tca cca cca cca tca tct ccc ccc t ca tcc ctc acc aca gat<br>Ile Val Ser Pro Pro Pro Ser Ser Pro Pro S er Ser Leu Thr Thr Asp<br>330 335 340 345 | 1121 |
| ccc agc cag tct cta ctc agc ctg gag caa g aa ccg ctg ttg tcc cgg<br>Pro Ser Gln Ser Leu Leu Ser Leu Glu Gln G lu Pro Leu Leu Ser Arg<br>350 355 360 | 1169 |
| atg ggc agc ctg cgg gct ccc gtg gac gag g ac cgc ctg tcc ccg ctg<br>Met Gly Ser Leu Arg Ala Pro Val Asp Glu A sp Arg Leu Ser Pro Leu<br>365 370 375 | 1217 |
| gtg gcg gcc gac tcg ctc ctg gag cat gtg c gg gag gac ttc tcc ggc<br>Val Ala Ala Asp Ser Leu Leu Glu His Val A rg Glu Asp Phe Ser Gly<br>380 385 390 | 1265 |
| ctc ctc cct gag gag ttc atc agc ctt tcc c ca ccc cac gag gcc ctc<br>Leu Leu Pro Glu Glu Phe Ile Ser Leu Ser P ro Pro His Glu Ala Leu<br>395 400 405 | 1313 |
| gac tac cac ttc ggc ctc gag gag ggc gag g gc atc aga gac ctc ttc<br>Asp Tyr His Phe Gly Leu Glu Glu Gly Glu G ly Ile Arg Asp Leu Phe<br>410 415 420 425 | 1361 |
| gac tgt gac ttt ggg gac ctc acc ccc ctg g at ttc tgacagggct<br>Asp Cys Asp Phe Gly Asp Leu Thr Pro Leu A sp Phe<br>430 435 | 1407 |
| tggagggacc agggtttcca gagtagctca ccttgtctct gcagccctgg a gcccctgt | 1467 |
| ccctggccgt cctcccagcc tgtttggaaa catttaattt ataccctct c ctctgtctc | 1527 |
| cagaagcttc tagctctggg gtctggctac cgctaggagg ctgagcaagc c aggaaggga | 1587 |
| aggagtctgt gtggtgtgta tgtgcatgca gcctacaccc acacgtgtgt a ccgggggtg | 1647 |
| aatgtgtgtg agcatgtgtg tgtgcatgta ccggggaatg aaggtgaaca t acacctctg | 1707 |
| tgtgtgcact gcagacacgc cccagtgtgt ccacatgtgt gtgcatgagt c catctctgc | 1767 |
| gcgtgggggg gctctaactg cactttcggc ccttttgctc gtggggtccc a caaggccca | 1827 |
| gggcagtgcc tgctcccaga atctggtgct ctgaccaggc caggtgggga g gctttggct | 1887 |
| ggctgggcgt gtaggacggt gagagcactt ctgtcttaaa ggttttttct g attgaagct | 1947 |
| ttaatggagc gttatttatt tatcgaggcc tctttggtga gcctggggaa t cagcaaaag | 2007 |
| gggaggaggg gtgtggggtt gataccccaa ctccctctac ccttgagcaa g ggcaggggt | 2067 |
| ccctgagctg ttcttctgcc ccatactgaa ggaactgagg cctgggtgat t tatttattg | 2127 |
| ggaaagtgag ggagggagac agactgactg acagccatgg gtggtcagat g gtgggtgg | 2187 |
| gccctctcca gggggccagt tcagggccca gctgccccc aggatggata t gagatggga | 2247 |
| gaggtgagtg ggggaccttc actgatgtgg gcaggagggg tggtgaaggc c tcccccagc | 2307 |
| ccagaccctg tggtccctcc tgcagtgtct gaagcgcctg cctccccact g ctctgcccc | 2367 |
| accctccaat ctgcactttg atttgcttcc taacagctct gttccctcct g ctttggttt | 2427 |
| taataaatat tttgatgacg ttaaaaaaaa | 2457 |

```
<210> SEQ ID NO 13
<211> LENGTH: 437
<212> TYPE: PRT
<213> ORGANISM: human

<400> SEQUENCE: 13

Met Ala Leu Ala Gly Ala Pro Ala Gly Gly Pro Cys Ala Pro Ala Leu
 1               5                  10                  15

Glu Ala Leu Leu Gly Ala Gly Ala Leu Arg Leu Leu Asp Ser Ser Gln
            20                  25                  30

Ile Val Ile Ile Ser Ala Ala Gln Asp Ala Ser Ala Pro Pro Ala Pro
        35                  40                  45

Thr Gly Pro Ala Ala Pro Ala Gly Pro Cys Asp Pro Asp Leu Leu
    50                  55                  60

Leu Phe Ala Thr Pro Gln Ala Pro Arg Pro Thr Pro Ser Ala Pro Arg
65                  70                  75                  80

Pro Ala Leu Gly Arg Pro Pro Val Lys Arg Arg Leu Asp Leu Glu Thr
                85                  90                  95

Asp His Gln Tyr Leu Ala Glu Ser Ser Gly Pro Ala Arg Gly Arg Gly
            100                 105                 110

Arg His Pro Gly Lys Gly Val Lys Ser Pro Gly Glu Lys Ser Arg Tyr
        115                 120                 125

Glu Thr Ser Leu Asn Leu Thr Thr Lys Arg Phe Leu Glu Leu Leu Ser
130                 135                 140

His Ser Ala Asp Gly Val Val Asp Leu Asn Trp Ala Ala Glu Val Leu
145                 150                 155                 160

Lys Val Gln Lys Arg Arg Ile Tyr Asp Ile Thr Asn Val Leu Glu Gly
                165                 170                 175

Ile Gln Leu Ile Ala Lys Lys Ser Lys Asn His Ile Gln Trp Leu Gly
            180                 185                 190

Ser His Thr Thr Val Gly Val Gly Gly Arg Leu Glu Gly Leu Thr Gln
        195                 200                 205

Asp Leu Arg Gln Leu Gln Glu Ser Glu Gln Gln Leu Asp His Leu Met
210                 215                 220

Asn Ile Cys Thr Thr Gln Leu Arg Leu Leu Ser Glu Asp Thr Asp Ser
225                 230                 235                 240

Gln Arg Leu Ala Tyr Val Thr Cys Gln Asp Leu Arg Ser Ile Ala Asp
                245                 250                 255

Pro Ala Glu Gln Met Val Met Val Ile Lys Ala Pro Pro Glu Thr Gln
            260                 265                 270

Leu Gln Ala Val Asp Ser Ser Glu Asn Phe Gln Ile Ser Leu Lys Ser
        275                 280                 285

Lys Gln Gly Pro Ile Asp Val Phe Leu Cys Pro Glu Glu Thr Val Gly
    290                 295                 300

Gly Ile Ser Pro Gly Lys Thr Pro Ser Gln Glu Val Thr Ser Glu Glu
305                 310                 315                 320

Glu Asn Arg Ala Thr Asp Ser Ala Thr Ile Val Ser Pro Pro Ser
                325                 330                 335

Ser Pro Pro Ser Ser Leu Thr Thr Asp Pro Ser Gln Ser Leu Leu Ser
            340                 345                 350

Leu Glu Gln Glu Pro Leu Leu Ser Arg Met Gly Ser Leu Arg Ala Pro
        355                 360                 365

Val Asp Glu Asp Arg Leu Ser Pro Leu Val Ala Ala Asp Ser Leu Leu
```

```
                    370             375             380
Glu His Val Arg Glu Asp Phe Ser Gly Leu L eu Pro Glu Phe Ile
385                 390             395                 400

Ser Leu Ser Pro Pro His Glu Ala Leu Asp T yr His Phe Gly Leu Glu
                405             410                 415

Glu Gly Glu Gly Ile Arg Asp Leu Phe Asp C ys Asp Phe Gly Asp Leu
            420             425                 430

Thr Pro Leu Asp Phe
        435

<210> SEQ ID NO 14
<211> LENGTH: 20
<212> TYPE: DNA
<213> ORGANISM: Artificial Sequence
<220> FEATURE:
<223> OTHER INFORMATION: Description of Artificial  Sequence:primer

<400> SEQUENCE: 14
gctctagagc ccagtataga                                              20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial  Sequence:primer

<400> SEQUENCE: 15
gctctagatg tctcaagcct ttccc                                        25

<210> SEQ ID NO 16
<211> LENGTH: 13
<212> TYPE: PRT
<213> ORGANISM: Artificial Sequence
<220> FEATURE:
<223> OTHER INFORMATION: Description of Artificial  Sequence:DP-3
      peptide to  raise antiserum

<400> SEQUENCE: 16

Asp Glu Glu Asp Glu Glu Glu Asp Pro Ser S er Pro Glu
 1               5                  10

<210> SEQ ID NO 17
<211> LENGTH: 15
<212> TYPE: PRT
<213> ORGANISM: Artificial Sequence
<220> FEATURE:
<223> OTHER INFORMATION: Description of Artificial  Sequence:DP-3
      peptide to raise antiserum

<400> SEQUENCE: 17

Val Ala Leu Ala Thr Gly Gln Leu Pro Ala S er Asn Ser His Gln
 1               5                  10                  15

<210> SEQ ID NO 18
<211> LENGTH: 17
<212> TYPE: DNA
<213> ORGANISM: Artificial Sequence
<220> FEATURE:
<223> OTHER INFORMATION: Description of Artificial  Sequence:primer

<400> SEQUENCE: 18
cacccgcaat ggtcact                                                 17
```

```
<210> SEQ ID NO 19
<211> LENGTH: 18
<212> TYPE: DNA
<213> ORGANISM: Artificial Sequence
<220> FEATURE:
<223> OTHER INFORMATION: Description of Artificial  Sequence:primer

<400> SEQUENCE: 19
atgtctcaag cctttccc                                                    18

<210> SEQ ID NO 20
<211> LENGTH: 19
<212> TYPE: DNA
<213> ORGANISM: Artificial Sequence
<220> FEATURE:
<223> OTHER INFORMATION: Description of Artificial  Sequence:primer

<400> SEQUENCE: 20
gatagaaaac gagctagag                                                   19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial  Sequence:primer

<400> SEQUENCE: 21
ttctgagaaa tcagagtcta                                                  20

<210> SEQ ID NO 22
<211> LENGTH: 11
<212> TYPE: PRT
<213> ORGANISM: Artificial Sequence
<220> FEATURE:
<223> OTHER INFORMATION: Description of Artificial  Sequence:DP-3 peptide

<400> SEQUENCE: 22

Ala Gly Trp Val Pro Ser Lys Arg Ser Lys L ys
 1               5                  10

<210> SEQ ID NO 23
<211> LENGTH: 22
<212> TYPE: DNA
<213> ORGANISM: Artificial Sequence
<220> FEATURE:
<223> OTHER INFORMATION: Description of Artificial  Sequence:cDNA
      splice of Figure 1

<400> SEQUENCE: 23
cccaggttgc attttagtga tg                                               22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial  Sequence:cDNA
      splice of Figure 1

<400> SEQUENCE: 24
agaaggtgag tttctagtaa a                                                21

<210> SEQ ID NO 25
<211> LENGTH: 27
<212> TYPE: PRT
<213> ORGANISM: Artificial Sequence
```

```
<220> FEATURE:
<223> OTHER INFORMATION: Description of Artificial  Sequence:DP-3
      pepide of Figure 1

<400> SEQUENCE: 25

Ala Gly Trp Val Pro Ser Asp Arg Lys Arg A la Arg Glu Phe Ile Asp
 1               5                  10                  15

Ser Asp Phe Ser Glu Ser Lys Arg Ser Lys L ys
             20                  25
```

We claim:

1. An assay for a regulator of cell cycle progression which comprises:
   (a) expressing in a cell a protein which is an E2F-1 transcription factor or portion thereof, which protein comprises a functional nuclear localization signal and which protein is capable of forming a heterodimer with a DP transcription factor or portion thereof;
   (b) expressing in said cell the DP transcription factor or portion thereof, wherein the DP transcription factor is selected from the group consisting of DP-3β and DP-3γ; and
   (c) determining the degree of nuclear localization of the protein in the presence and absence of a putative regulator, wherein a difference in the degree of nuclear localization in the presence and absence of the putative regulator indicates that the putative regulator is a regulator of cell cycle progression.

* * * * *